US011430245B2

(12) United States Patent
Zyglowicz et al.

(10) Patent No.: US 11,430,245 B2
(45) Date of Patent: Aug. 30, 2022

(54) URINATION PREDICTION AND MONITORING

(71) Applicant: GOGO Band, Inc., Ashland, VA (US)

(72) Inventors: Steven Zyglowicz, Leesburg, VA (US); Tim Baker, Beaverdam, VA (US); Jon Coble, Glen Allen, VA (US); Israel Franco, Chappaqua, NY (US)

(*) Notice: Subject to any disclaimer, the term of this patent is extended or adjusted under 35 U.S.C. 154(b) by 0 days.

(21) Appl. No.: 16/896,857

(22) Filed: Jun. 9, 2020

(65) Prior Publication Data
US 2020/0302201 A1 Sep. 24, 2020

Related U.S. Application Data

(63) Continuation of application No. 15/485,057, filed on Apr. 11, 2017, now Pat. No. 10,685,249.
(Continued)

(51) Int. Cl.
G06V 40/10 (2022.01)
G16H 10/65 (2018.01)
(Continued)

(52) U.S. Cl.
CPC ............... *G06V 40/10* (2022.01); *G06K 9/62* (2013.01); *G06V 40/20* (2022.01); *G16H 10/65* (2018.01); *G16H 40/63* (2018.01); *G16H 50/50* (2018.01)

(58) Field of Classification Search
CPC ........... G06K 9/00885; G06K 9/00335; G16H 50/50; G16H 40/63; G16H 10/65
(Continued)

(56) References Cited

U.S. PATENT DOCUMENTS 6,579,247 B1 6/2003 Abramovitch et al.
7,977,529 B2 7/2011 Bergman et al.
(Continued)

FOREIGN PATENT DOCUMENTS

CN 103445770 A 12/2013
JP 7255764 A 10/1995
(Continued)

OTHER PUBLICATIONS

Office Action for U.S. Appl. No. 15/485,046, dated Feb. 10, 2020.
(Continued)

*Primary Examiner* — John A Tweel, Jr.
(74) *Attorney, Agent, or Firm* — Nixon Peabody LLP

(57) ABSTRACT

A system for predicting and detecting urination events of users is disclosed. The system can include any number of wearable devices, mobile devices, hubs, computing devices, and servers to collect, share, process, and interpret data, as well as to provide stimuli to users and caregivers. Biometric and/or environmental data associated with a user can be collected and applied to a urination model to determine a predicted urination time. The user or a caregiver can be provided with direct or environmental stimuli conveying information about predicted urination times. Ongoing biometric and/or environmental data collection can be used to identify, and provide stimuli warning of, imminent urination events. Voluntary and involuntary feedback of actual urination events, as well as continued biometric and/or environmental data collection, can be used to train individual and collective urination models.

21 Claims, 8 Drawing Sheets

Related U.S. Application Data

(60) Provisional application No. 62/365,714, filed on Jul. 22, 2016, provisional application No. 62/321,690, filed on Apr. 12, 2016.

(51) Int. Cl.
  *G16H 50/50* (2018.01)
  *G16H 40/63* (2018.01)
  *G06K 9/62* (2022.01)
  *G06V 40/20* (2022.01)

(58) Field of Classification Search
  USPC .......................................................... 706/12
  See application file for complete search history.

(56) References Cited

U.S. PATENT DOCUMENTS

| | | | |
|---|---|---|---|
| 8,204,597 B2* | 6/2012 | Gerber | ............... A61N 1/36007 607/41 |
| 8,648,727 B2 | 2/2014 | Caldwell et al. | |
| 8,664,467 B2 | 3/2014 | Roe et al. | |
| 10,685,249 B2* | 6/2020 | Zyglowicz | ............... G06K 9/62 |
| 2003/0084906 A1 | 5/2003 | Roe | |
| 2003/0117296 A1 | 6/2003 | Seely | |
| 2008/0294047 A1 | 11/2008 | Kodama et al. | |
| 2011/0004123 A1 | 1/2011 | Companion | |
| 2012/0172783 A1 | 7/2012 | Harris et al. | |
| 2013/0023786 A1 | 1/2013 | Mani et al. | |
| 2014/0275849 A1 | 9/2014 | Acquista | |
| 2016/0120455 A1 | 5/2016 | Pop et al. | |
| 2016/0125759 A1 | 5/2016 | Daugherty et al. | |
| 2017/0290540 A1 | 10/2017 | Franco | |
| 2017/0293846 A1 | 10/2017 | Zyglowicz et al. | |
| 2018/0214122 A1 | 8/2018 | Ansell et al. | |
| 2018/0353119 A1 | 12/2018 | Nakanishi et al. | |

FOREIGN PATENT DOCUMENTS

| | | | |
|---|---|---|---|
| JP | 2005087543 A | 4/2005 | |
| JP | 2014079506 A | 5/2014 | |
| KR | 10-2013-0040876 | 4/2013 | |
| KR | 1020140141425 A | 12/2014 | |
| WO | 2011125003 A1 | 10/2011 | |
| WO | 2013095231 A1 | 6/2013 | |
| WO | 2017180661 | 10/2017 | |

OTHER PUBLICATIONS

Canadian Office Action for CA Application No. 3020748, dated Aug. 15, 2019.
European Supplementary Search Report for EP Application No. 17783007.2, dated Oct. 24, 2019.
U.S. Appl. No. 15/485,046 , "Non-Final Office Action", dated Jun. 10, 2019, 29 pages.
Kelley , "Evaluation of Voiding Dysfunction and Measurement of Bladder Volume", Reviews in Urology, vol. 6, Suppl 1, 2004, pp. S32-S37.
Niu et al., "Design of an Ultrasound Bladder Volume Measurement and Alarm System", 5th International Conference on Bioinformatics and Biomedical Engineering, May 2011, pp. 1-4.
PCT/US2017/027065 , "International Preliminary Report on Patentability", dated Oct. 25, 2018, 8 pages.
Petrican et al., "Design of a Miniaturized Ultrasonic Bladder Volume Monitor and Subsequent Preliminary Evaluation on 41 Enuretic Patients", IEEE Transactions on Rehabilitation Engineering, vol. 6, No. 1, Mar. 1998, pp. 66-74.
PCT/US2017/027065, "International Search Report and Written Opinion", dated Jun. 21, 2017, 12 pages.
KR Notification of Reason of Refusal for Application No. 10-2018-7032633, dated Sep. 28, 2021.
KR Written Opinion for Application No. 10-2018-7032633, dated Sep. 5, 2021.
JP Written Opinion for Application No. 2018-554491, dated Jun. 9, 2021.
JP Office Action for Application No. 2018-554491, dated Mar. 2, 2021.
JP Decision to Grant for Application No. 2018-554491, dated Nov. 12, 2021.
Israel Office Action for Application No. 262263, dated Jun. 18, 2020.
CN Second Office Action for Application No. 2017-80036246, dated Dec. 2, 2021, with CN Search Report dated Nov. 24, 2021.
CN First Office Action for Application No. 2017-80036246, dated Apr. 2, 2021.
U.S. Office Action for U.S. Appl. No. 15/485,057, dated Feb. 11, 2020, 14 pp.
U.S. Notice of Allowance for U.S. Appl. No. 15/485,057, dated Apr. 9, 2020, 9 pp.
AU Examination Report for Application No. 2017249318, dated Apr. 6, 2021.
ID Office Action for Application No. 201847042203, dated Nov. 2, 2021.
U.S. Notice of Allowance for U.S. Appl. No. 15/485,046, dated May 10, 2020, 9 pp.
Tarvainen, M. et al., "User's Guide", Kubios HRV, Jul. 6, 2012, 44 pp., MATLAB, Kuopio, Finland.

* cited by examiner

URINATION PREDICTION AND MONITORING

CROSS REFERENCE TO RELATED APPLICATIONS

The present application is a Continuation of U.S. Non-Provisional application Ser. No. 15/485,057 filed Apr. 11, 2017 and entitled "URINATION PREDICTION AND MONITORING," which claims the benefit of U.S. Provisional Application No. 62/365,714 filed Jul. 22, 2016 and entitled "URINATION PREDICTION AND MONITORING," and also claims the benefit of U.S. Provisional Application No. 62/321,690 filed Apr. 12, 2016 and entitled "BEDWETTING TRAINING DEVICE AND METHOD," all of which are hereby incorporated by reference in their entirety.

TECHNICAL FIELD

The present disclosure relates to prediction of physiological events generally and more specifically to the prediction of urination, such as in individuals suffering from enuresis.

BACKGROUND

Many individuals suffer from some form of enuresis or involuntary urination. Pediatric enuresis is especially prevalent, such as nocturnal bedwetting or diurnal involuntary urination. Pediatric enuresis is one of the most prominent chronic children's health conditions, affecting over 200 million children worldwide. Enuresis can present physical and psychological health concerns for a suffering individual.

Current treatments for enuresis involve either drug treatment or the use of enuresis alarms. Drug treatment temporarily blocks urine/bladder function and are associated with high rates of relapse and severe side effects including seizures and cardiotoxicity. Diurnal alarm systems provide alerts based on static intervals throughout the day, reminding a user to either urinate or perform a self-check for the need to urinate. Nocturnal alarm systems rely on moisture sensors to detect the presence of excess moisture. These systems are generally difficult to use, prone to breakage, and not kid-friendly.

Nocturnal alarm systems generally rely on unwieldy, unreliable, and uncomfortable detection technology. For example, some alarm systems incorporate a moisture sensor into a bed to provide an alarm when the bed has been sufficiently wetted by involuntary urination. Such systems, however, only trigger upon the release of substantial amounts of fluid, providing notice to the suffering individual or caregiver only after substantial urination has occurred. Thus, any remedial actions taken in response to an alarm can only occur a substantial amount of time after urination begins, and thus individuals and caregivers are relegated to only responding after involuntary urination occurs.

Some alarm systems rely on large sensors attached to an individual's undergarments and relay data by a wired or wireless connection. The large sensors can be uncomfortable for a user, can detach or be inadvertently removed during sleep, and can require placement at locations distant from the source of the urination. Wired connections can hinder a user's ability to sleep and can cause potential tangling hazards. Existing sensors using wireless connections require large batteries and circuitry to last throughout the night.

There is a need to provide improved tools for combating enuresis to caregivers and individuals suffering from enuresis.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
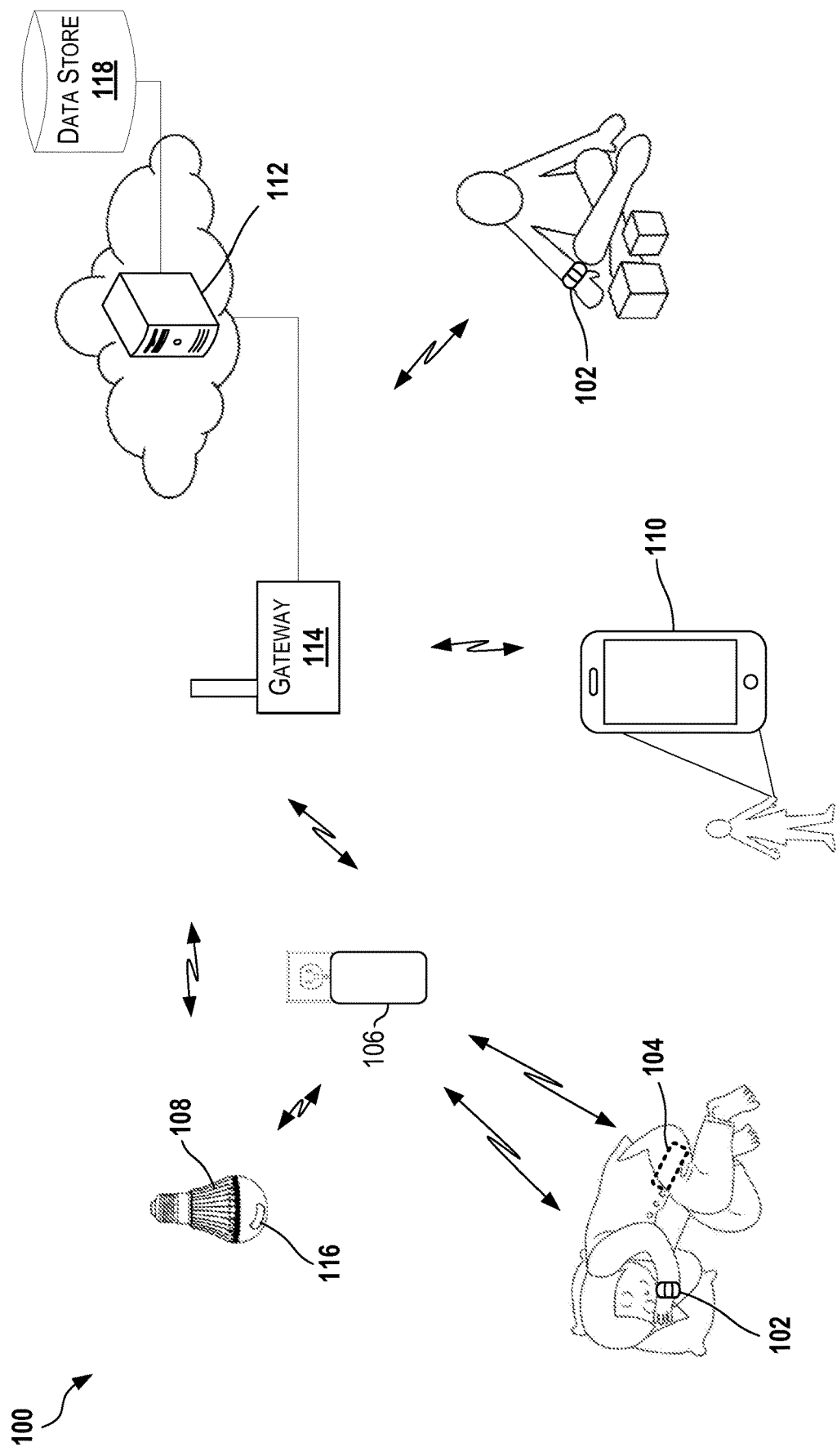
FIG. 1 is a schematic diagram depicting a urination detection and prediction ecosystem according to certain aspects of the present disclosure.

Certain aspects and features of the present disclosure relate to an overall system, as well as methods, for detecting or predicting a urination event, such as with children (e.g., below age 18, from ages 5 to 18, or from ages 2 to 5) or with geriatric individuals (e.g., above age 55). Biometric data and/or environmental data associated with an individual can be collected and used to predict the occurrence of a urination event (e.g., an intentional or unintentional micturition or an urge to micturate) or an expected urination time. Urination prediction data can be collected from a wearable device, such as a wearable band or any other suitable device for collecting biometric data from a user or environmental data from an environment in which the user is or may be located. The telemetry data (e.g., biometric and/or environmental data) can be processed using stored data and/or stored algorithms to determine whether a urination urge exists or to predict when a urination urge may soon exist. The stored data and/or stored algorithms can be based on general predictive models. In some cases, the stored data and/or stored algorithms can be based on customized predictive models that are customized, in advance or in real-time (e.g., real-time, approximately real-time, rapidly, or as fast as reasonably possible), to an individual user. Upon detecting a urination urge or determining that a urination urge may soon exist, an action can be taken, such as providing an alarm or alert, providing signals or updates to user devices, network devices, and/or cloud devices, or performing other actions. Examples of collected telemetry data include heart rate, body temperature, skin conductivity, motion, food intake, liquid intake, blood pressure, level of sleep, and others. A patch sensor can be used with or without the wearable telemetry device to provide urination detection. The patch sensor can be an active or passive radio-frequency identification (RFID) tag suitable for detecting moisture. In some cases, the patch sensor can be a Bluetooth low energy (BTLE) module coupled to a moisture detection circuit. The patch sensor can be read from a nearby reader, such as a nearby hub or a computing device (e.g., smartphone). An RFID-based or BTLE-based patch sensor can allow the sensor to have a very small form factor, needing very little or no complex circuitry and/or battery power. The small form factor of such patch sensors can allow the sensor to be placed in ideal locations (e.g., on an undergarment adjacent the source of urination) and allow the sensor to be worn without discomfort or fear of damage. A reader or hub can periodically read the patch sensor or can receive updates from the patch sensor. The reader or hub can perform an action when a moisture event is detected. The actions performable by the reader or hub can include sending alarms or alerts, providing signals or updates to user devices, network devices, and/or cloud devices, or performing other actions. In some cases, patch sensors can be single-use or multi-use disposable sensors. In some cases, the patch can be waterproof. In some cases, a patch can be battery powered (e.g., user-replaceable or non-user-replaceable) and can operate in a low power mode until sufficient moisture is detected.

Control of one's urination and bladder function can involve first learning to recognize the bladder full signal from the brain and then exercise control of one's bladder. These functions may be learned through behavioral conditioning processes. Certain aspects and features of the present disclosure can improve a user's ability to learn bladder control.

The advance notice provided by the intelligent predictive alarming system can provide an individual or caregiver with improved control over enuresis, potentially avoiding inadvertent urination altogether. Further, the advance notice can aid individuals in proper behavioral conditioning, which can speed cure rates and decrease relapse rates. The unique form factor of the patch sensor can allow the sensor to be worn more easily, thus improving patient compliance. Further, the small form factor of the patch sensor can allow the sensor to be placed in opportune locations and can allow the sensor to provide immediate feedback at the very first sign of excess moisture, rather than needing to wait for substantial wetting to occur. The earlier alarm available due to the patch sensor can reduce damage and embarrassment due to enuresis and can improve an individual's ability to be behaviorally conditioned. Cure rates can be sped up and relapse rates can be decreased.

In some cases, telemetry data (e.g., biometric and/or environmental data) from the wearable device can be further analyzed for other predictive factors. For example, telemetry data may be analyzed to determine a likelihood of suffering from a future symptom or condition, such as anaphylactic shock, an asthma attack, migraines, insomnia, cardiac issues, Tourette syndrome tics, hydration states of the body, opioid addiction, states of suicide or depression, or sleep apnea.

In some cases, generating a prediction of an event, such as an imminent need to urinate, can use one or a combination of machine learning algorithms and heuristic rules. The heuristic rules can be specific to a user (e.g., based on a user's fluid intake, a user's last urination event, a user's weight, etc) and/or can be generic (e.g., prediction based on an overall average time between alarm based on cross-user data).

As used in various embodiments herein, collected data may include raw data that has been collected from one or more sensors or may include processed data based on that raw data. Processed data can be processed or analyzed in any suitable form using one or more processors, such as processors in a data collection device or in a separate processing device. In some cases, processing or analyzing data can include applying transforms to the data in the frequency and time domains, as well as other domains. In some cases, wavelet transforms can be applied to process or analyze data as necessary. In an example, the measurement of heart rate data can include raw, analog sensor data collected from light sensors; a first set of data processed from the sensor data and representing individual pulses over time; a second set of data processed from either the sensor data or the first set of data and representing average heart rates over time; and a third set of data processed from any of the previous data and representing heart rate variability over time.

In some cases, data collection (e.g., biometric data collection) can occur in realtime. Data can be pre-processed and windowed, so as to perform analysis of the data over a subset of data points (e.g., based on a number of samples, a period of time, or a number of domain events, such as oscillations). In some cases, data from any sensor or suitable source of data as described herein can be collected, analyzed, and/or otherwise processed in any suitable sample size, including 1, 2, 4, 8, 16, 32, 64, 128, 256, 512, or other numbers of samples.

In some cases, a user or caregiver can access, control, or otherwise interact with the wearable telemetry device or a patch sensor using a computing device, such as a computer, smartphone, dedicated controller, or other such device. In some cases, a user can provide feedback through a computing device or through the wearable device, which can be stored and used to improve future predictions. Such feedback can include when a urination urge is felt, when a urination event occurs (e.g., inadvertent or intentional), when a prediction is correct, when a prediction is incorrect, an amount of fluid consumed, or any other suitable feedback.

Certain aspects of the present disclosure relate to collecting biometric data of a user through one or more wearable devices worn by the user and optionally collecting environmental data of a space occupied by or proximate to the user through a hub, a wearable device, a local mobile computing device, or any other device. These pieces of collected data can be collected over time to generate a biological function model used to predict or anticipate the expected time one or more biological functions may occur. Prediction can occur offline or in realtime. The systems can predict both the occurrence of biological functions (e.g., the occurrence of urination) as well as urges related to biological functions (e.g., an urge to urinate). While the present disclosure can be used in relation to any suitable biological function, the disclosure will hereinafter refer to the predictions related to urination, such as prediction of a urination event. A urination event can be the occurrence of intentional or unintentional micturition.

A user model can be generated or updated based on the collected data (e.g., biometric or environmental data). As used herein, the terms user model or user urination model can mean a model for predicting urination that is associated with a user, such as through the user of a user identifier (e.g., a unique identifier). Therefore, applying data to a user model can result in a predicted urination time and/or a chance of urination as a function of time. The user model can be used to predict and/or sense an upcoming user-related urination event. The user model can make such predictions based on any suitable combination of current, historical, and/or recent (e.g., a subset of historical data having a sufficiently high degree of predictive weight, such as data from the past few hours) collected data. Data applied to a user model to make a prediction can be applied in subsets, or windows, of data, such as data from the past 64, 128, or 256 samples, data from the past 1, 5, 10, 20, or 30 seconds, or data from any domain of events. Other numbers of samples and/or time frames can be used. Upon making a prediction, alerts and/or notifications can be presented—dynamically, in real-time—to any combination of a user, a caregiver, or a device (e.g., a hub, a computing device, a computer, or a server), among others. In particular, the system can incorporate various hardware and software elements that cooperate to implement various methods and techniques for collecting user biometric and environmental data over time; for modeling a physiological state (e.g., pending urination) of a user based on the collected data; for inferring projections of future events related to the physiological state of the user (e.g., a particular set of time windows in which the user will predictably have a urination event); for preemptively presenting these projections to the user and/or a caregiver of the user (e.g., a parent, a grandparent, or a babysitter), such as through a smartphone, tablet, smartwatch, or other computing device associated with the caregiver; and for preemptively affecting the user by presenting stimulus to the user—directly or indirectly—such as via light, sound, vibration, temperature change or some other stimuli.

The system can include an external server (e.g., an application server) that stores user data and user-related environmental data. Such data can be associated with an account assigned to the user, such as through a unique user identifier. The system can include one or more wearable devices incorporating various sensors capable of measuring various user biometrics (e.g., heart rate, motion, or other biometric data mentioned herein) and a wireless transmitter that uploads this biometric data to the user's account (e.g., within a remote database linked to the application server), such as through a hub or through an external computing device (e.g., a user's or caregiver's smartphone or tablet) associated with the user's account. The system can also include a hub, which may incorporate various sensors that detect environmental conditions (e.g., temperature, humidity, light level, and noise level) and a wireless transmitter for uploading collected environmental condition data to one or more users' account(s), such as through a local Wi-Fi router or other network connection. The application server can apply the received biometric and environmental condition data to a current urination model associated with the user to determine and output predictions for updates to the user's urination model, such as a particular time window during which the user will likely have a urination event. The application server can also store received biometric and environmental condition data over time and can generate new urination models or update (e.g., retrain) existing user-specific urination models specific to the user over time as new user-related data is collected and received. In some cases, a hub and/or a native application executing on a computing device linked to the hub and/or to the user's account can execute the disclosed methods and techniques, such as when a connection with an application server is temporarily unavailable or without the need for an application server.

The system can further generate a collective urination model (e.g., baseline urination model) generic to and available for use (e.g., initial use or continued use) by a population of users based on historical data collected over time from users in that population or other relevant populations of users. In some cases, users can participate and provide data (e.g., collected biometric and/or environmental data, voluntary and/or involuntary feedback, demographic information, or other data) to aid in generating baseline urination models. A baseline urination model can be applied to a particular user to predict future urination events related to the user. For example, a baseline urination model can be applied to the user if sufficient data (e.g., biometric or environmental) specific to the user is not currently available or extant, such as when the user's account is first activated, to enable rough predictions of future urination time windows of the user to be made during a first use of the system. In this example, once a sufficient dataset is collected from the user, such as after a first week of use of the system, the system can generate a new user-specific urination model based on the collected data.

In some cases, the prediction of urination events for a particular user can make use of multiple models, such as a baseline urination model and a user urination model. Transfer learning can be leveraged to improve the prediction of urination events of a new user or an established user. In some cases, predicating urination events can involve applying multiple models, such as one or more baseline urination models and a user urination model, with individual weightings applied to each model. For a new user, a baseline urination model may initially be highly weighted whereas the user urination model is not highly weighted. However, as more data associated with the user is received, the user urination model can be trained and the weighting factors can shift so that the baseline urination model becomes less heavily weighted while the weighting of the user urination model increases. In some cases, where multiple baseline urination models can exist for different sub-populations of users, prediction of an individual user's urination event can include using multiple sub-population baseline urination models, associated with sub-populations to which the user belongs, each having different weightings, such as weightings corresponding to the degree to which the individual belongs to or fits within each sub-population.

Elements of the system can be implemented on one or more computer networks, computer systems, applications servers, or other suitable devices. The computer system can include one or more cloud-based computer(s), one or more mainframe computer system(s), one or more grid-based computer system(s), or any other suitable computer system(s). The computer system can support collection of data as described herein, such as from a wearable device and/or a hub; processing of the collected data; and transmission of alerts, notifications, stimuli, and/or user interface updates to one or more devices linked to or associated with the user's account. For example, the computer system can receive user biometric data and distribute alerts and notifications over a distributed network, such as over a cellular network or over an Internet connection. In this example, the computer system can send alerts and notifications to a native user monitoring application executing on a user's or caregiver's computing device (e.g., smartphone, tablet, computer, or other suitable device). As used herein, alerts and notifications can include status updates, commands, information, or any suitable signal.

In some cases, one or more computing devices associated with the system (e.g., associated with the user's account)—such as a laptop computer, a desktop computer, a tablet, a smartphone, a personal data assistant (PDA), or other suitable device—can maintain information related to the user's account; can create and maintain a user-specific physiological model associated with the account; and can execute a monitoring application to generate, receive, and/or display alerts and notifications and/or update physiological state change predictions for presentation to a user or caregiver.

In one example, the system can track biometric data (e.g., heart rate, motion, sleep quality, and the like) of the user and environmental conditions near the user during the user's sleeping periods. The system can dynamically, in real-time, processes a urination model assigned to or generated specifically for the user based on collected biometric and/or environmental data associated with the user to infer and/or revise a predicted time that the user will likely urinate while sleeping. In some cases, the system can dynamically, in real-time, update a visual interface rendered on a user's or caregiver's computing device according to the inferred and revised predicted times that the user will urinate. In some cases, the system can additionally or alternately present a stimulus to the user and/or caregiver, such as by increasing light in the user or caregiver's environment (e.g., by turning on or increasing brightness of a lamp or by opening automatic blinds), by presenting a sound (e.g. alarm or other waveform) in the user or caregiver's environment, or by issuing a vibration at the user or caregiver (e.g., vibrating a wearable device, vibrating a chair or bed, or vibrating any structure in physical contact with the user or caregiver) just prior to the predicted urination event.

By performing this functionality on a consistent or regular basis and by dynamically updating the user-specific urination model based on collected biometric and/or environmental data, which can include urination detection through the urination detection sensor disclosed herein, the system can provide reliable and effective remediation of, or even cure of, nighttime enuresis (both pediatric and geriatric forms for night time). Even periodic or one-time use of the system may be beneficial.

In some cases, the system can operate in an offline mode using one or more devices carried by, worn by, or in proximity of a user when connection to the Internet, an application server, or a hub or base station is unavailable. In an offline mode, one or more devices, such as wearable devices and computing devices, can operate independently or in communication with one another. Prior to entering an offline mode, a device (e.g., wearable device or smartphone) can obtain and store a current urination model and/or predicted urination time(s), such as from an application server. For example, a wearable band can automatically download (e.g., by requesting information or receiving a push notice) a current urination model and/or predicted urination time via a hub while the user is in range of the hub. When in the offline mode, the device can operate based on the stored model or prediction(s) to provide notices, alarms, stimuli, or the like. In some cases, the device(s) can continue to collect data that can be processed with the stored model and/or prediction(s) to generate updated predicted urination time(s) (e.g., as altered based on newly collected data). The updated predicted urination time(s) can be used to provide notices, alarms, stimuli, or the like. In some cases, even if the device is operating in an online mode (e.g., where connection to the application server is available), the device may nevertheless rely on stored models and/or prediction(s) to conserve bandwidth and/or power, for example at least until the end of an expiration period, until a notification is received of an available updated model and/or prediction, or until a determination is made that the accuracy of the stored model and/or prediction time is below a minimum threshold.

In some cases, upon receiving a stimulus or not, a user can provide voluntary feedback to the system. Feedback can be provided using an interface on any suitable device, such as a wearable device or a computing device. In an example, a stimulus received by a wearable device can signal the user to perform a self-check to determine if the individual has a need or urge to urinate. The user can provide feedback, such as positive feedback indicating a need or urge to urinate exists or negative feedback indicating no such need or urge exists, via an interface of the wearable device (e.g., button(s), accelerometers, capacitive sensors, or other interface elements). In another example, a user can independently perform a self-check or can independently realize a need or urge to urinate, in which case the user can also provide feedback. In another example, a user can provide feedback when a urination event has occurred, such as by performing a series of taps on the wearable device after urination. In some cases, voluntary feedback associated with the user can be provided by a third party, such as by a caregiver (e.g., via a smartphone or tablet), such as after interrogating the user regarding a need or urge to urinate or witnessing a urination event.

In some cases, involuntary feedback can be provided to the system. Involuntary feedback can be any feedback that can be automatically received (e.g., without the user intentionally manipulating a user interface for the purposes of providing feedback) and that provides confirmation or a degree of confirmation of the accuracy of a predicted event (e.g., predicted urination time). Involuntary feedback can take the form of or be based on direct data or inference data. Direct data can include any data from a device designed to directly detect the occurrence of the predicted event. For example, direct data can include data from a urination detection sensor placed in a user's undergarments or on a user's body, which can provide confirmation that a urination event has or has not occurred. Inference data can be any data that can be highly correlated with occurrence of the predicted event. For example, inference data can include any combination of location-based data of a device associated with the user indicating that the user has entered and/or remained in a bathroom (e.g., for at least a predetermined period of time), pH data from a urinal or toilet likely to be used by the user (e.g., pH data optionally filtered to only include data associated with a time period at or near a predicted urination time of the user), occupancy sensor data associated with a bathroom likely to be used by a user (e.g., occupancy data optionally filtered to only include data associated with a time period at or near a predicted urination time of the user), or any other suitable data that may be highly correlated with occurrence of the predicted event. In some cases, a sensor at, in, or proximate a bathroom can identify the presence of a wearable device associated with a user to provide an indication that the user is at or using the bathroom. In some cases, the system can use voluntary feedback to help train the correlative values associated with various sources or types of inference data.

Feedback can be used to make alterations to predicted urination time(s), such as a next predicted urination time or a set of future predicted urination times. Feedback can also be used to update the user-specific model, such as a stored user model available to a wearable device in an offline mode, or the user-specific model maintained by an application server or hub. Feedback can thus be used locally by a device (e.g., a wearable device operating in offline mode), locally by multiple devices (e.g., via communications between a wearable device and a hub or smartphone), or by an application server or other cloud-based device. When used by a device other than the device generating the feedback signal, the feedback can be received in any suitable form, such as a feedback signal, instructions for modifying a model or predicted urination time(s), or a model or predicted urination time(s).

In some cases, alternatively or additionally to initiating stimulus based on a predicted urination time, a stimulus can be initiated (e.g., to indicate an imminent urination event) based on current sensor data received from one or more sensors in, on, or adjacent to a user. The current sensor data can be used to independently make a determination of an imminent urination event, or can be used in combination with a model and/or predicted urination time to make the determination. For example, a wearable device can detect biometric data (e.g., heart rate change or skin conductivity change) and provide a stimulus indicative of an imminent urination event. Thus, the system can operate to both predict and sense future urination events.

As described herein, a computing device, such as a mobile device, can perform some or all of the same functions as a hub with regards to communicating information to the application server; calculating and updating urination models; collecting additional sensor data; and updating and notifying a caregiver of events, predicted events and how the user is performing throughout the day.

By performing this functionality on a consistent basis and by dynamically updating the user-specific urination model based on collected biometric and/or environmental data, as well as voluntary and involuntary feedback, the system can provide reliable and effective remediation of, or even cure of, daytime enuresis (both pediatric and geriatric forms). Even periodic or one-time use of the system may be beneficial. In some cases, the system can also act as a bladder control training solution, such as for potty training.

In some cases, biometric data can include measurements of bladder contents, such as how full a bladder may be. However, in some cases, biometric data can include various types of biometric data other than bladder measurements. In such cases, predictions can be generated without the need to directly measure the bladder (e.g., without measuring bladder fullness).

In some cases, the system disclosed herein can make use of accounts to identify users and/or caregivers. In some cases, an account system can include administrative accounts given access to setup further accounts, control user-defined settings, control access to devices, make purchases, and perform other functions. Administrative accounts can be set up as not associated with any biometric data or environmental data, but can be used primarily for performing administrative functions. In some cases, administrative accounts can access and manipulate data and/or devices associated with one or more user accounts. Administrative accounts may be suitable for caregivers. In some cases, no administrative accounts may be used and administrative functions may be performed by user accounts.

A user account can be established for each user that will be monitored for urination prediction. A user account can be associated with hubs, wearable devices, urination sensors, controllable appliances (e.g., light sources), controllable sounds sources, and other devices. Data collected from any associated component can be associated with the user (e.g., using a user identifier). The application server can utilize the association between data and user to ensure data can be tracked to particular users and to ensure the data can be processed as desired (e.g., to generate or update user-specific models). A user may associate various components (e.g. use multiple wearable devices, or a device may be replaced) over the user's lifetime, but the data generated by an associated device (e.g., while the device is associated with the user) can remain associated with the user. A history of components associated with a particular user can be maintained. In some cases, user accounts can perform the various administrative functions described above with reference to administrator accounts.

In an example, a caregiver with two users (e.g., parent with two children) may set up an administrative account for the caregiver and two user accounts: one for each user. The caregiver may obtain devices and associate each device to a respective user. In some cases, a single device (e.g., a hub) may be able to associate with multiple users. In another example, a single individual may set up both a user account and an administrative account for the individual. In yet another example, a single individual may set up a user account with administrative privileges for the individual.

In some cases, a computing device, such as a mobile device (e.g., smartphone or tablet) can be used to perform some, most or all of the actions associated with an administrative account or a user account. The computing device can run an application (e.g., web application or native application) that allows a user to interface with any of the devices of the system, such as wearable devices and an application server. In some cases, the application can present various information to a user or caregiver, such as predicted urination events, imminent urination events, actual events, and other data. The application can generate various stimuli, such as to indicate when a user should perform a self-check or when a caregiver should check on a user. The application can allow visualization of raw or processed data, as well as the ability to access and/or manipulate device-specific data and/or settings. The application can store and/or visualize historical data, current data, and projected data. In some cases, the application can compare a user's data to the data from other users, such as other users being cared for by the same set of caregivers or anonymized data for any other users. Additionally, the application can include a virtual coach or assistant to provide feedback, tips, and/or information to users or caregivers to achieve better results with the system. The various functions of the application can be incorporated into native applications or web applications accessible through any suitable device, such as computers and purpose-built devices (e.g., a hub or wearable device with such enhanced functionality).

It has been determined that certain aspects of the present disclosure are significantly more effective at treating and curing enuresis than current non-drug-based treatments. For example, the average user cure rate for pediatric enuresis using certain aspects of the present disclosure is twice as high as current non-drug-based treatments.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram depicting a urination detection and prediction ecosystem 100 according to certain aspects of the present disclosure. The ecosystem 100 can include any number of networked devices, such as wearable devices 102, urination detection sensors 104, hubs 106, network-controllable appliances 116, computing devices 110, application servers 112, and any other suitable device (e.g., other sensors for monitoring an individual or an environment). The networked devices may be connected to one another directly, connected to a local area network, connected to a logical network encompassing more than one local area network, and/or connected to the Internet, such as to a cloud. The networked devices may send transmissions to and from one another or to and from a cloud server (e.g., application server 112) to effectuate various aspects disclosed herein. An application server 112 can be a single computing device or multiple computing devices in communication with one another (e.g., a grid computing environment). In some cases, devices in a local area network can communication with one another and/or with the cloud via a gateway 114 or router.

In an example, a wearable device 102 can be a device suitable for collecting biometric data from a user, such as a wearable device (e.g., a wristband, a watch, or a patch). Biometric data can include data related to an individual. In some cases, biometric data can further include data related to a user's environment. Examples of collectable biometric data can include heart rate, motion, ambient temperature, body temperature, blood oxygenation, skin conductivity, blood pressure, electrocardiogram data, electroencephalogram data, electromyographic data, respiration rate, sleep quality, depth of sleep, restfulness, or heart rate variability data. In some cases, collectable biometric data can include user input, such as a button press on a wearable device to indicate a urination event, a urination urge, a lack of a urination event, or a lack of a urination urge, among others. Other types of biometric data can be collected. In some cases, biometric data can be collected using sensors positioned on, embedded within, or otherwise physically associated with the wearable device 102. In some cases, external sensors in continuous, intermittent, or on-demand communication with the wearable device 102 or other network devices can collect biometric data for use by the ecosystem 100 or any devices of the ecosystem 100. In an example, biometric data may be collected from a group of devices, including a wearable device 102 (e.g., wristband), a urination detection sensor 104 via a hub 106, light and sound sensors within the hub 106, a network-connected scale (not shown) and a smartphone-connected blood pressure monitor (not shown) via a smartphone (e.g., computing device 110).

Various aspects of the present disclosure can be performed by any appropriate device in the ecosystem 100, however in some cases the bulk of the data processing can be performed by an application server 112 accessible through the cloud (e.g., accessible through any standard Internet connection). Biometric data collected by the various sensors and devices can be uploaded to the application server 112 for processing to predict an expected urination time based on a user model. The data, expected urination time, and user model can all be associated with a user identifier indicative of the individual from which the biometric data is collected and to which the expected urination time applies. An individual's user model for predicting urination can be initially populated using existing aggregate data from other users, existing models, any combination thereof, or other sources. The individual's user model can be initially populated with or without respect to user input and/or collected biometric data associated with the user.

In an example case, a user may be sleeping with a wearable device 102 and a urination detection sensor 104. Biometric data can be collected by the wearable device 102 and continuously or periodically uploaded to an application server 112 for processing. The application server 112 can determine when a urination event is expected to occur (e.g., by determining the time at which point the likelihood of a urination event surpasses a minimum threshold) based on the user's model stored on the application server 112. The application server 112 can transmit the expected urination time to the wearable device 102 and/or a caretaker's computing device 110 upon determining the expected urination time. In some cases, the application server 112 can wait until a desired interval prior to the expected urination time (e.g., 15 minutes, 10 minutes, 5 minutes, 2 minutes, 1 minute, 30 seconds, or any other suitable time frame) and then transmit an update or alert. In some cases, an update or alert can invoke a stimulus on the wearable device 102, such as a noise, vibration, display, or other discernable stimulus. The stimulus can alert the user to the impending urination event. In some cases, an update or alert can cause a network-controllable appliance 116 (e.g., controllable light bulb) to perform a function, such as causing a network-controllable light bulb to activate and/or change to a desired color or intensity or to cause a network-controllable sound source 108 (e.g., a speaker) to provide an auditory stimulus, such as a music file or any suitable sound. In some cases, an update or alert can cause a computing device 110 (e.g., a caretaker's computing device or a user's computing device) to invoke a stimulus, such as a noise, vibration, display, or other discernable stimulus, alerting the caretaker or user of the impending urination event. In some cases, when the application server 112 transmits the expected urination time to the wearable device 102 upon determining the expected urination time, the wearable device 102 can continue monitoring current biometric data and dynamically update the expected urination time according to the current biometric data. Additionally, when an unintentional urination event occurs, the urination detection sensor 104 may provide urination occurrence feedback accessible by another network device, such as a hub 106 or the wearable device 102. In some cases, an RFID-based or BTLE-based urination detection sensor 104 can be read by a hub, which can relay the urination occurrence feedback to another device, such as the application server 112. The application server 112 can use the urination occurrence feedback, optionally along with collected and/or current biometric data, to improve the user model stored in the application server 112.

A user or caregiver may be able to access current, future, or past predictions of expected urination times, historical urination events (e.g., detected as well as manually input), historical and current biometric data, and other information through the ecosystem 100. Such information may be accessible via any suitable computing device, such as a smartphone, smartwatch, laptop computer, desktop computer, wearable device 102, or other device. The information can be accessed from an application server 112 or can be stored locally by one or more local devices. In some cases, predictions of expected urination times can be utilized by a computing device 110 (e.g., smartphone) of a user or caregiver and shared with or integrated within other applications running on the computing device 110. For example, predictions of expected urination times can be automatically embedded within a calendar application to help an individual suffering from enuresis or a caregiver plan out future engagements or travel. Predictions of expected urination times can also be made available to third-party software via the application server 112 using an application programming interface (API).

It will be understood that the actions performable by the application server 112 may be performed by any device of the ecosystem 100, including a single external or internal server or a cluster or group of external or internal servers.

In some cases, a network-controllable appliance 116 can include a controllable light source. A hub 106 or computing device 110 can control the light source using any suitable communication protocol (e.g., WiFi or BTLE). Alerts, notifications, or other signals originating from any device of the ecosystem 100 can be used (e.g., by a hub 106 or computing device 110) to control the network-controllable appliance 116. In some cases, the network-controllable appliance 116 can communicate with an application server 112 without the need for a hub 106 or computing device 110.

As an example, a light source can be controlled to raise the ambient light in an environment at a time associated with a predicted urination event. Such illumination of the environment can serve multiple purposes, including waking a sleeping user to prompt an intentional self-check as to whether need or urge to urinate exists; prompting an awake user to perform a self-check; waking and/or prompting a caregiver to attend to a user; and providing a caregiver sufficient ambient light to inspect or attend to a user. For example, having a room already lit, potentially in the middle of the night, when a caregiver comes to check on a user associated with a potentially imminent urination event can facilitate the caregiver's duties. Further, automatic illumination of the environment by the system can provide feedback indicative that the signal is functioning properly. In some cases, the light source can be modulated or further controlled (e.g., to a defined light level or color) to convey additional information, such as whether an alert pertains to a predicted, imminent, or previously-occurred urination event.

In some cases, a network-controllable sound source 108 can be controlled similarly to how the network-controllable appliance 116 is controlled. For example, the system can control the network-controllable sound source 108 to generate an auditory stimulus, such as a noise, music, voice, or another sound. In some cases, the auditory stimulus can provide additional information, such as information pertaining to the type of event (e.g., predicted, imminent, or previously-occurred) and any other information. Information can be provided through associated sounds, stored sound files (e.g., stored voice sounds), or dynamically generated voice sounds.

In some cases, the system can be used as an alarm to wake a sleeping individual regardless of any predictions. Such an alarm can make use of a network-controllable sound source 108 or any suitable network-controllable appliance 116. Such an alarm can be based on saved times (e.g., a user setting a time to wake up), saved durations (e.g., a user setting a timer for how long they wish to sleep), biometric data (e.g., generate an alarm when light sleep is detected), environmental data (e.g., generate an alarm when a sufficient light level is detected), any other rules or data, or any combination thereof.

In some cases, the application server 112 can include any number of physical or virtual servers, load balancers, firewalls, networking components (e.g. switches), data storage servers, and other general purpose computing equipment. The application server 112 can be self-hosted by a user or caregiver, hosted by a company operating the application server 112 and directly associated with the ecosystem 100, or hosted by a third party solution (e.g. Google Cloud™ or Microsoft Azure™) that maintains the equipment associated with application server 112, but is not directly associated with the ecosystem 100.

The application server 112 can include a data store 118. The data store 118 can include program information, stored biometric data, stored environmental data, stored generic models, stored user-specific models, collective (e.g., baseline) models, algorithms, user information, device information, encryption keys, and any other data necessary for operating the ecosystem 100 or other aspects of the present disclosure. The application server 112 can process data associated with an individual user, with a group of users (e.g., a group of users associated with a single caregiver or group of caregivers), with a population (e.g., a group of users sharing similar traits), or with the full corpus of users (e.g., all user data available to the application server 112).

The application server 112 can use various machine learning algorithms and techniques for selecting optimal models and for updating models. The application server 112 can operate on a supervised learning model, allowing collected data to be used to further improve prediction capabilities. For example, the application server 112 can receive data associated with a user, including biometric data, environmental data, voluntary feedback, and involuntary feedback. The data can be time-stamped (e.g., based on an actual time or a relative time) or can be analyzed for timing correlations. The application server 112 thus has access to the predictive data (e.g., data used by the application server 112 to generate predictions) and the actual classifications (e.g., feedback of actual urination events) it is trying to predict. The application server 112 can thus apply the predictive data and classifications to the various machine learning techniques to generate and/or update models to optimize model accuracy. In some cases, machine learning techniques can further be used to optimize speed of prediction and/or other variables. Supervised learning operations can be triggered by the arrival of data, can be run at specific time intervals, or can be otherwise initiated (e.g., automatically run when demands on the application server 112 are low or below a threshold). Further, the application server 112 can also host standard applications (e.g. web application reachable via secured or unsecured hypertext transfer protocol). Such other applications can allow users and/or caregivers to register their associated devices, purchase additional devices, and/or perform other actions or interactions.

Figure 2:
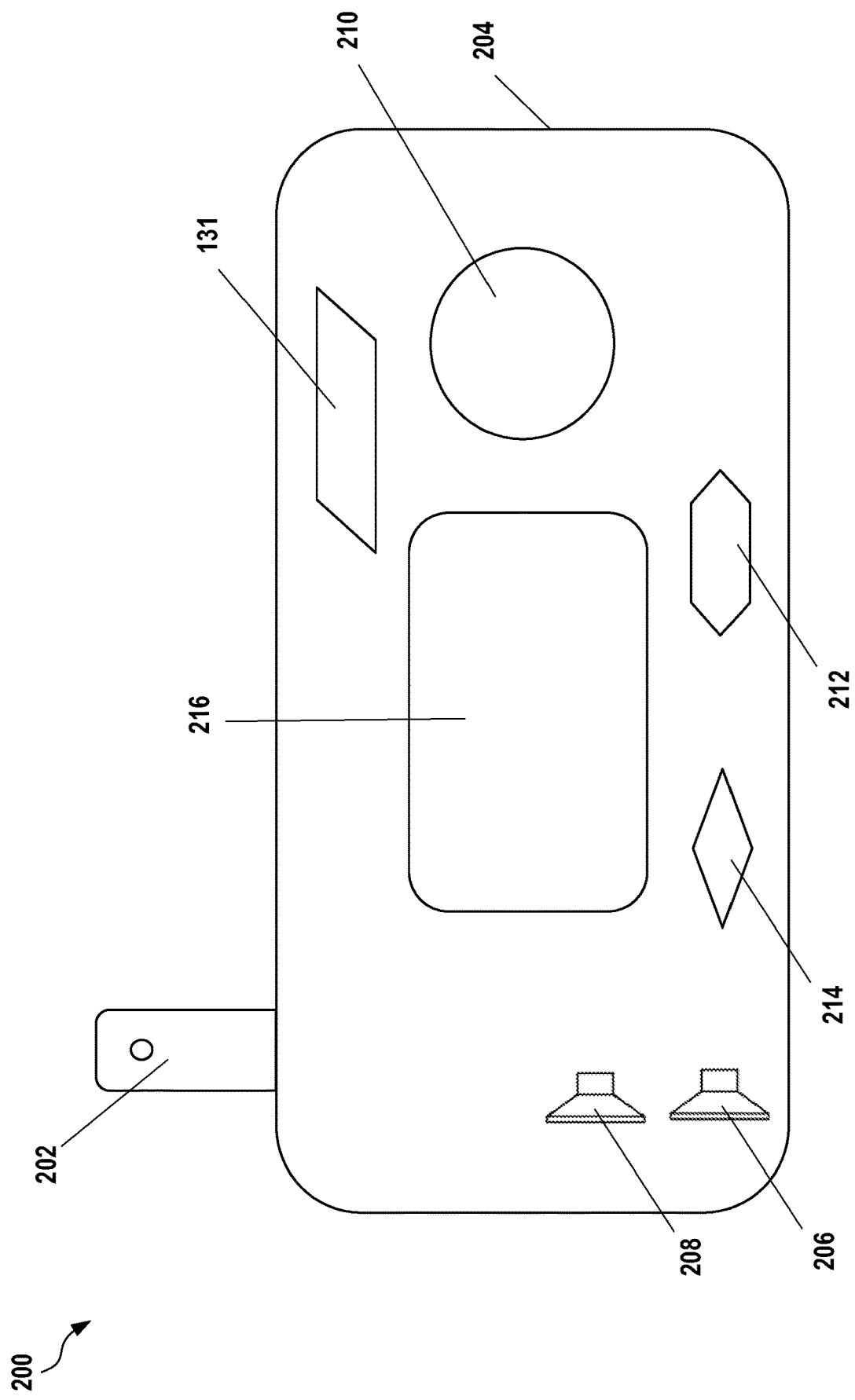
FIG. 2 is a schematic diagram of a hub according to certain aspects of the present disclosure.

FIG. 2 is a schematic diagram of a hub 200 according to certain aspects of the present disclosure. Hub 200 can be hub 106 of FIG. 1. Hub 200 can support any suitable wired or wireless communication standard for communicating with wearable devices, a local network, and/or the Internet. For example, hub 200 can include radios suitable for BTLE communication, WiFi communication, and/or RFID communication. Hub 200 can communicate with any number of wearable devices (e.g., wearable device 102 of FIG. 1), sensors (e.g., urination detection sensor 104 of FIG. 1), network-controllable appliances (e.g., network-controllable appliance 116 of FIG. 1, such as a controllable light source), network-controllable sound source (e.g., network-controllable sound source 108 of FIG. 1), an application server (e.g., application server 112 of FIG. 1), and a computing device (e.g., computing device 110 of FIG. 1, such as a smartphone or tablet). The hub 200 can be a computing device and can contain capabilities typically found in modern computers (e.g. processor 131, memory, user interface, power source, input and output capabilities). The hub 200 can process information coming from any connected system components. Such information can be proxied from or through various other system components, as well as being processed and enhanced. The hub 200 can process received data to transform it into data suitable for controlling the system (e.g., processing received data to generate instructions for updating a user model), for storage (e.g., processing received data to generate biometric data and/or inferences based on received data), or for any other suitable use. The hub 200 can be associated with one or more users (e.g., identified through unique user identifiers) and can associate received or processed data with the one or more users.

The hub 200 can optionally apply data compression and/or encryption prior to sending data (e.g., to an application server). Data compression can reduce the amount of information that is sent to the application server, thus minimizing used bandwidth. Encryption (e.g., public/private key asymmetric cryptography) can protect data from interception. Since an application server can be located in a third party cloud solution, data being transmitted between the application server and the hub 200 may be sent over insecure networks and across unknown distances, thus data compression and/or encryption may be beneficial and desirable. In some cases, connected components can offload compression and/or encryption tasks or duties to the hub 200, minimizing the processing power and energy used by the components. For example, a wearable device can transmit uncompressed and/or unencrypted data to the hub 200, which can then compress and/or encrypt the data prior to relaying the data to another device, such as an application server.

In some cases, the hub 200 can be powered from a power source 202. Suitable power sources include mains power (e.g., 120 volt alternating current), rechargeable or non-rechargeable battery power, or any other suitable power source. In some cases, a hub 200 can incorporate multiple power sources 202, such as mains power and a rechargeable battery, allowing the rechargeable battery to be recharged when the hub 200 is connected to mains power and allowing the hub 200 to operate for a duration when disconnected from mains power (e.g., to move the hub to another location, such as near a bed when sleeping). Power control circuit within the hub 200 can adapt power provided through the power source 202 to a desired output (e.g., direct current suitable for operating the internal circuitry of the hub 200). In some cases, the hub 200 can provide power to charge another device (e.g., wearable device 102 of FIG. 1) or charge a removable power source of another device (e.g., the hub 200 can include a dock for charging a swappable battery of a wearable device or a battery-powered urination detection sensor). In one example, the hub 200 can recharge another device using a universal serial bus (USB). In another example, the hub 200 can recharge another device via inductive charging.

In some cases, the hub 200 can send data (e.g. a sound waveform) to any connected system components in either bidirectional or unidirectional fashion. For example, a system component may use only the advertising solution of BTLE communication. Sufficient information may be included in the advertising data for the hub 200 to determine or infer a state associated with the system component. In another example, a system component can use bidirectional communication (e.g., using the full protocol of BTLE) to allow the hub 200 to read and write data associated with the component. In some cases, the hub 200 can use bidirectional communication to set up a component to transmit notifications upon detection of an event.

The hub 200 can include an enclosure 204 to protect certain electronic components. The hub 200 may contain a sound source 206 (e.g., speaker, vibration motor, or other acoustic transducer) to generate audible stimuli. The hub 200 may include a speaker to generate sounds (e.g. voice, music, generic sounds) that can provide an alert or information to a user or caregiver. In one example, a caregiver can send audio information directly to the hub 200 to present sounds to a user within auditory range of the hub 200.

The hub can include a microphone 208 suitable for recording sounds occurring in the general proximity to the hub, which sounds may be presumably occurring in proximity of a user or caregiver generally proximate the hub 200. With a microphone 208 and a speaker 206, the hub 200 can provide bidirectional (e.g., full-duplex or half-duplex) voice communication between the hub 200 and another computing device. In one example, a caregiver can use a smartphone to communicate with a user proximate the hub 200. In some cases, the hub 200 can receive and interpret audio signals from the microphone 208 to perform commands or transmit signals to other components of the system. Adding speech to text, action, or intent software, the system may be able to perform actions based on the voice commands received at the hub 200. Such voice commands can be initiated when a button 210 is pressed and/or with a particular audio signal is detected, among other ways. Speech software may be stored on the hub 200, an application server, another system component, or any combination thereof.

The hub 200 can also include an ambient temperature sensor 212 to collect temperature data associated with the environment in which the hub 200 is situated, which may presumably be the environment of the user in some cases. The hub 200 may also contain an ambient light sensor 214 to detect light level data associated with the environment in which the hub 200 is situated, which may presumably be the environment of the user in some cases. The hub 200 can further include additional environmental sensors. Data collected by the hub 200 can be associated with a user's account (e.g., a user identifier).

The hub 200 can also include a display 216. The display 216 can be any suitable display, such as a full color display (e.g. organic light emitting diode or liquid crystal display) or a simple collection of discreet light emitters. The display 216 can incorporate a user interface, such as a touch-sensitive interface (e.g., capacitive touch sensing), capable of receiving interactions from the user.

The hub 200 can also include one or more buttons 210 for user input. A button 210 can be used to interpret instructions from the user, such as instructions to initiate commands, perform actions, change stored values, or simply cycle through information presented on the display 216.

In some cases, some or all of the various functions of the hub 200 can be performed by an application running on a computing device, such as a smartphone, tablet, or personal computer. In some cases, a computing device can be used to perform all desired functions without requiring the use of a hub 200.

Figure 3:
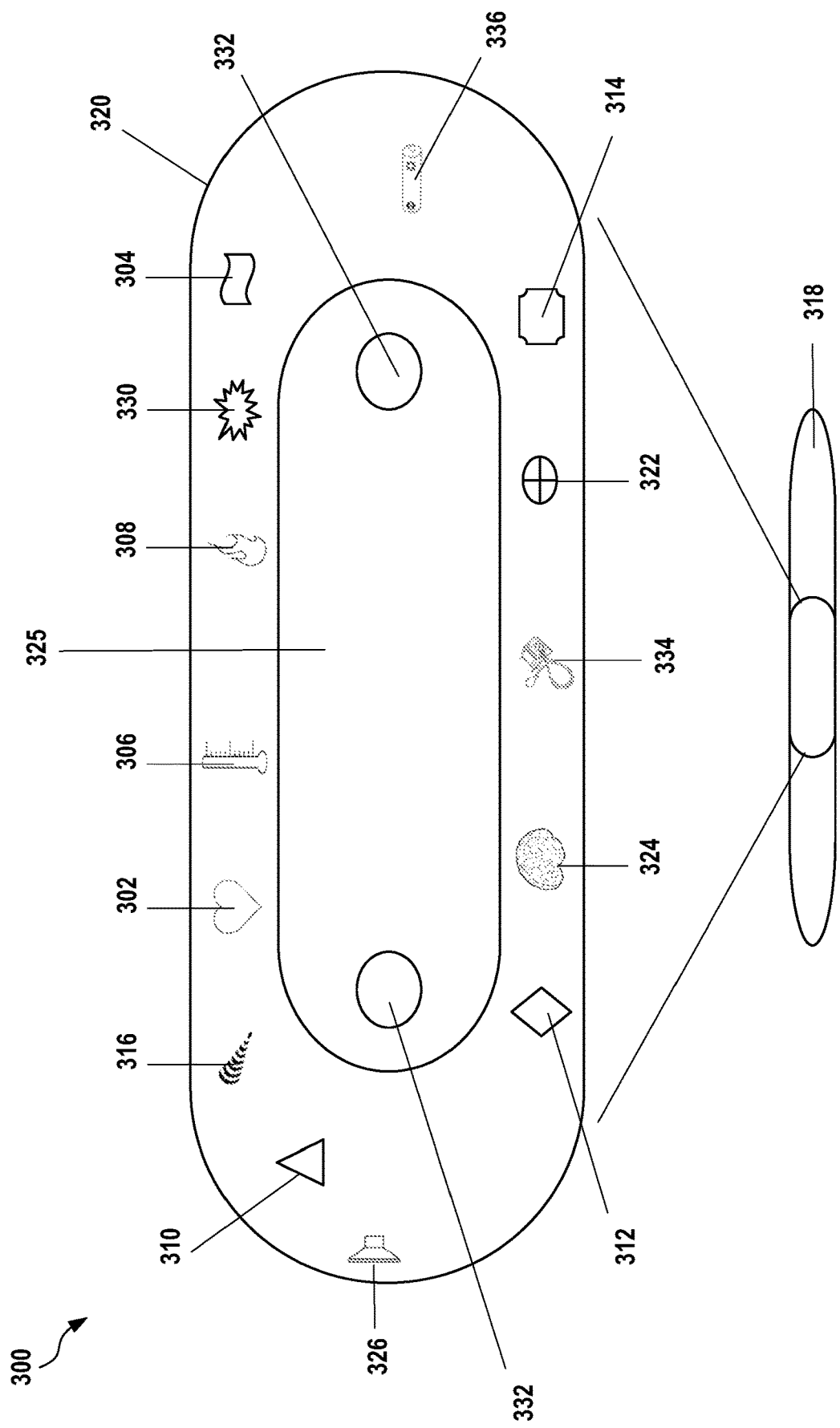
FIG. 3 is a schematic diagram of a wearable device according to certain aspects of the present disclosure.

FIG. 3 is a schematic diagram of a wearable device 300 according to certain aspects of the present disclosure. The wearable device 300 can be a wearable device 102 of FIG. 1. A wearable device 300 can include one or more sensors, such as a heart rate sensor 302, a motion sensor 304 (e.g. accelerometer or gyroscope), a body temperature sensor 306, an ambient temperature sensor 308, a skin conductivity sensor 310, an electrocardiogram (e.g., ECG) sensor 312, an electroencephalogram (e.g., EEG) sensor 314, a blood pressure sensor 334, and any other suitable sensors. Wearable device 300 can also perform local processing (e.g., applying algorithms) to obtain further biometric data, such as heart rate variability data. Wearable device 300 can include wired or wireless communication equipment, such as a wireless transceiver 316. The wearable device 300 can collect various biometric data from the user, collect environmental data, process collected data, transmit processed or unprocessed data to other devices such as a hub or computing device, and perform other tasks.

The wearable device can include a band 318, such as a food-safe or skin-safe (e.g., silicone) band containing or supporting a module housing 320. The sensors, wireless transceiver 316, a battery 336, and other related or necessary components can be supported by and/or contained within the module housing 320 and optionally the band 318. For example, skin conductivity sensor 310 can include sensing circuitry within the housing 320 electrically coupled to sensors within the band 318. The housing 320 and/or band 318 can provide dust-resistant, dust-proof, water-resistant, and/or water-proof containment. The band 318 can be adjustable in size to allow the wearable device 300 to be worn by differently sized individuals or the same individual who may grow over time, as well as to allow placement of the wearable device 300 in various locations (e.g., wrist, arm, ankle, thigh, waist, chest, toe, or ear). In some cases, the band 318 can be removable or replaceable. In some cases, the housing 320 can be inserted into a pocket of the band 318, yet in other cases the band 318 attach to the housing 320. In some cases, the housing 320 can be used without the band 318, such as with another attachment mechanism (e.g., adhesive patch or chest belt).

The wearable device can also include a processor 322 for performing various actions disclosed herein. The processor 322 can compress, analyze, filter, timestamp, or otherwise manipulate data collected through sensors integrated into or otherwise accessible (e.g., via wired or wireless communication) to the wearable device 300. Such actions can be taken prior to transmitting the sensor data to another device, such as a hub and/or local computing device, although unprocessed sensor data can be sent as well.

The wearable device 300 can also include volatile and/or non-volatile memory 324 for storing information such as firmware, urination models, urination model inputs, urination model outputs, biometric data, derived biometric data, urination time windows, predicted urination times, urination events including attributes and date/timestamp, user input information, user defined data, environmental data, and various other types of data. The memory 324 can store instructions enabling the processor 322 to perform actions described herein.

The wearable device 300 can also include a display 325. The display 325 can be any suitable display, such as a full color display (e.g. organic light emitting diode or liquid crystal display) or a simple set of discreet light emitters. The display 325 can incorporate a user interface, such as a touch-sensitive interface (e.g., capacitive touch sensing), capable of receiving interactions from the user.

The wearable device 300 can also include a sound generating source 326 (e.g. speaker). The sound generating device can be used to alert the user or provide audible feedback (e.g. accepting user input). In some cases, the wearable device 300 can further include a microphone.

The wearable device 300 can also include a vibration mechanism 330. The vibration mechanism 330 can provide vibrational alerts, auditory alerts, and/or tactile feedback (e.g. accepting use input).

The wearable device 300 can include one or more buttons 332 for user input. A button 332 can be used to interpret instructions from the user, such as instructions to initiate commands, perform actions, change stored values, or simply cycle through information presented on the display 325.

In some cases, a heart rate sensor 302 can include one or more optical emitters and one or more optical detectors that cooperate to optically detect heart pulses of the user on which the wearable device 300 is installed. Different frequencies of light can be used to perform better with respect to skin tone or darkened areas like tattoos. The frequencies can be selected by a user during a setup phase (e.g., by selecting light or dark skin tone) or can be determined automatically (e.g., by analyzing sensor data). Heart rate data can be collected periodically (e.g. 1 Hz or 0.2 HZ), continuously, or on demand. An analysis of heart rate data by the urination model or other algorithm as it is being captured substantially in real-time or post capture can be used to predict an impending or future urination event.

The wearable device 300 can also include a motion sensor 304 (e.g accelerometer or gyroscope) to capture motion and orientation data associated with the user. Motion data can be used as input into the processor 322 to calculate an activity measurement which can be used to correlate motion and movement with urination events. Motion data can be used to refine the calculation of the heart rate data to account for user motion. Motion data can be collected periodically, continuously, or on demand. An analysis of motion data by the urination model or other algorithm as it is being captured substantially in real-time or post capture can be used to predict an impending or future urination event. In another example, a motion sensor 304 can be used to detect muscle fasciculation (e.g., muscle twitches) of the user. Muscle twitching, both visible and invisible to the eye, can involve muscle contractions in the body distinguishable by a motion sensor 304. Muscle twitching can be an indication of impending or future urination event and can be used by the urination model to predict an impending or future urination event.

The motion sensor 304 can also act as an input device. In one example, the user can tap the wearable device 300 in a single or series of taps. The motion sensor 304 can sense these taps and provide the motion data to the processor 322, which can discern whether the motion data is indicative of a user tap pattern (e.g., one or more taps), in which case the processor 322 can perform an action based on the detected tap pattern. For example, an action can be to store information (e.g. log a urination event) or signal the hub (e.g., hub 200 of FIG. 2) and/or application server (e.g., application server 112 of FIG. 1).

In some cases, heart rate data and motion data can be used to categorize light sleep and deep sleep conditions while a user is sleeping. Light and deep sleep can be indicators of when a urination event may occur. The urination model can use this sleep data to sense when an impending urination event is likely to occur.

The wearable device 300 can also include a body temperature sensor 306, such as an infrared thermometer, a resistance thermometer, a silicon bandgap temperature sensor, or a thermistor. The sensor 306 can be positioned to be near or in contact with the skin of a user wearing the wearable device 300, which can provide more effective data capture. Body temperature data can be collected periodically (e.g. 1 Hz or 0.2 HZ), continuously, or on demand. An analysis of body temperature data by the urination model or other algorithm as it is being captured substantially in real-time or post capture can be used to predict an impending or future urination event.

The wearable device 300 can further include an ambient temperature sensor 308. The sensor 308 can be positioned to sense the temperature of ambient air without being affected by the heat of the user, such as being positioned on a side of the housing 320 facing away from the skin of a user wearing the wearable device 300. Ambient temperature data can be collected periodically (e.g. 1 Hz or 0.2 HZ), continuously, or on demand. An analysis of ambient temperature data by the urination model or other algorithm as it is being captured substantially in real-time or post capture can be used to predict an impending or future urination event.

The wearable device 300 can also include a skin conductivity sensor 310. The sensor 310 can be positioned on the wearable device 300 to be near or in contact with the skin of a user wearing the wearable device 300. Skin conductivity data can be collected periodically (e.g. 1 Hz or 0.2 HZ), continuously, or on demand. An analysis of skin conductivity data by the urination model or other algorithm as it is being captured substantially in real-time or post capture can be used to predict an impending or future urination event.

The wearable device 300 can also include an electrocardiogram (ECG) sensor 312. Electrocardiogram data can be collected periodically (e.g. 1 Hz or 10 HZ), continuously, or on demand. The sensor 312 can be used to calculate heart rate and can be used separately or in combination with the heart rate sensor 302 to improve the overall quality and/or accuracy of the heart rate data, as well as to calculate heart rate variability. In addition, ECG data can provide indicators of stress, fatigue, heart age, breathing index and mood. An analysis of the ECG data by the urination model or other algorithm as it is being captured substantially in real-time or post capture can be used to predict an impending or future urination event.

The wearable device 300 can also include a electroencephalogram (EEG) sensor 314. EEG data can be collected periodically (e.g. 1 Hz or 10 HZ), continuously, or on demand. EEG data can include brainwave information that can be used to detect brainwave patterns. These patterns can be indicative of attention, meditation, eye blink, ear twitch, muscle contraction, or any other repeatable action or state having a distinguishable brainwave pattern. In addition, the EEG data can provide information about delta, theta, low alpha, high alpha, low beta, high beta and gamma waves of the brain. EEG data can be used in determining rapid eye movement (REM) and non-REM sleep states, as these sleep states can be highly correlated with urination events. Analysis of EEG data by the urination model or other algorithm as it is being captured substantially in real-time or post capture can be used to predict an impending or future urination event.

Since there may be multiple sensors on the wearable device 300, the biometric data collected from a particular sensor and the derived or processed data from processing this data according to various algorithms, can be used independently or in conjunction with data from other sensors to optimize analysis and prediction. Analysis via the urination model or other algorithm can either be performed entirely on the wearable device 300, partially on the wearable device 300 and partially on another computing device (e.g. hub, computer such as a mobile device or application server) or fully on another computing device. The results can be stored on any combination of the wearable device 300, hub, computer such as a mobile device or application server, or elsewhere.

The processor 322, in conjunction with the memory 324, can be used to store biometric data, environmental data, and derived data even when the wearable device 300 is not in connection with a hub or computing device (e.g. mobile device), thus allowing data to persist until the wearable device 300 re-establishes a connection with another device (e.g., hub or application server) and is able to offload (e.g., sync) the data to the other device or to an application server. Additionally, the memory 324 can store information, such as predicted urination time windows for the user, so that the wearable device 300 can provide alarms or feedback (e.g. vibrations) when these time windows are approaching, imminent, ongoing, or passed, even when the wearable device 300 is not connected to a hub or computing device (e.g mobile device). The processor 322 can also leverage biometric data and/or environmental data to determine whether the wearable device 300 is properly positioned on the user. In some cases, such data can also be used to determine how a wearable device 300 must be maneuvered in order to properly or optimally position the wearable device 300 on the user. When not properly positioned on a user, the wearable device 300 can provide feedback to the user and/or to a caregiver. In some cases, when not properly positioned on a user, the wearable device 300 can enter a low power mode where any number of features, sensors, or operations are left unpowered or halted until a command is received, the wearable device 300 is power cycled or reset, a correction movement is sensed, or a period of time has passed.

The wearable device 300 can also contain a battery 336 or other power supply to power the sensors, memory 324, processor 322, and other electronic components of the wearable device 300. The battery 336 may include rechargeable (e.g. lithium-ion or lithium polymer) or non-rechargeable battery technology. In some cases, a battery 336 that is rechargeable may be recharged by removing the housing 320 from the band and, either directly or via a tether, attaching the housing 320 to a charging station, such as a portion of a hub. However, the battery 336 may be charged in any other suitable charging technique based on the battery technology or integrated battery charging electronics, such as through an internal dynamo, through magnetic induction, or through swappable batteries.

The wearable device 300 can include wireless communication capabilities to transfer information to and from a hub, a computing device (e.g. mobile device), and/or an application server (e.g., directly or through a proxy such as a hub). The wearable device 300 can also be physically docked to a hub, a computer (e.g. mobile device) and/or an application server to transmit data using a wired communication (e.g. Universal Serial Bus). During docking, the wearable device 300 may also recharge its rechargeable battery 336.

The wearable device 300 can include an associated unique identification (UID) suitable for identifying the source of the biometric information. This UID can be further associated with a user wearing the device, via a software application, pairing protocol or other mechanism. With a valid association, data collected from the wearable device 300 can be associated with the user. The wearable device 300 could be used on multiple different users over time, but might only be used with a single user at any particular time. In some cases, the wearable device 300 can prepare collected data by associating the UID or a user identifier to the collected data. In some cases, the wearable device 300 does not associate a user identifier to the collected data, rather another device is able to associate the user identifier with the UID of the device, and through that association be able to track that a particular user identifier belongs with a particular set of data associated with that UID. The association of biometric data and derived information can be used to update a user's personalized urination model and other algorithms. A UID can also be used to facilitate establishing wireless connections or transmitting data after a connection is established.

The wearable device 300 can maintain an actual or relative time clock that can be used to timestamp collected data. The clock can be updated via communication with another device such as a hub, computing device (e.g. mobile device), or application server. The clock information can be sent with other data through the communication protocols. The hub, computing device (e.g. mobile device), or application server can then modify (e.g. correct) the data to more accurately reflect a global clock so that the system may be synchronized to for accuracy despite small variations between different devices.

The wearable device 300 can enter different states of operation to optimize the functionality of the wearable device 300 and optimize user experience. For example, the wearable device 300 can detect when biometric data samples are not being collected. At that point, the wearable device 300 can conserve power by alerting the user via its user interface or by sending a signal to another device. The wearable device 300 can enter a low power mode to conserve power. Upon user request or receipt of some other stimulus (e.g. via a wireless signal transmitted from a computing device or a hub), the wearable device 300 can begin capturing biometric data or environmental data, and if successful, enter a normal operation state. If unable to capture data, the wearable device 300 can re-enter a low power state or can wait a predetermined period of time before performing the same capture test to attempt to enter a normal operation state.

The wearable device 300 can also enter a setup state to facilitate configuration of the wearable device 300. The setup state can be entered when the wearable device 300 is initially used, on demand, or at random times throughout the lifetime of the wearable device 300. Additionally, the wearable device 300 can enter a charging state when the user connects the wearable device 300 to a suitable charging mechanism (e.g., wired or wireless). The wearable device 300 may reduce power to certain components or may otherwise attempt to reduce power usage when in the charging state so that the rechargeable battery may be recharged at a faster rate.

Figure 4:
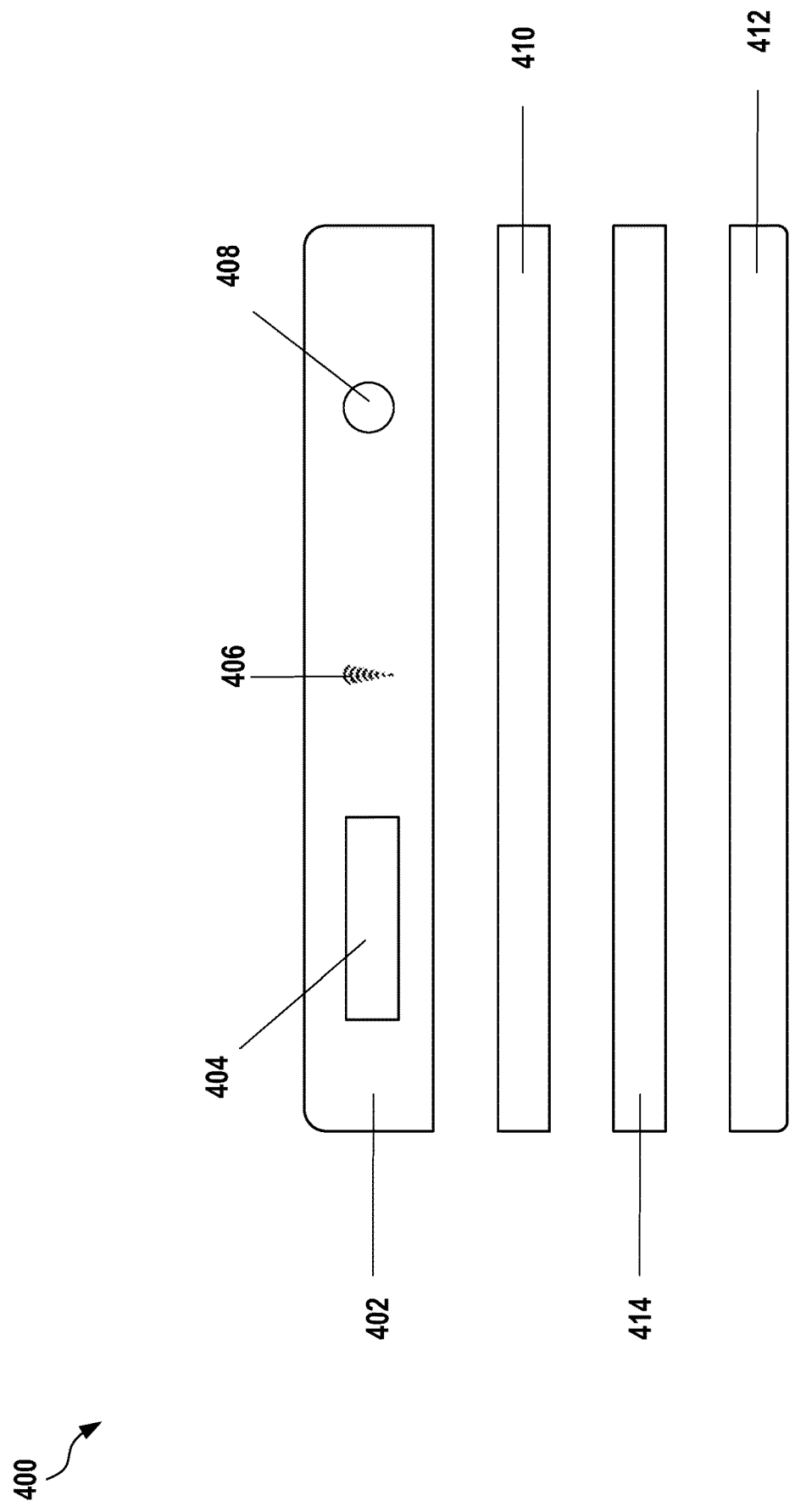
FIG. 4 is a schematic diagram depicting a urination detection sensor according to certain aspects of the present disclosure.

FIG. 4 is a schematic diagram depicting a urination detection sensor 400 according to certain aspects of the present disclosure. The sensor 400 can be designed to be attached to a user, a user's clothing, or another surface (e.g., a bed). The sensor 400 can optimally be placed on a user or on a user's clothing in the general area where urination would quickly accumulate (e.g. underwear, pajama bottom) if a urination event were to occur. The sensor 400 can include a reusable base 402 that optionally contains a power source 404, a display 408 (e.g., light emitting diode for indicating when the device is powered and/or connected), and a wireless antenna 406. The reusable base 402 can be coupled to a connection mechanism 410. The connection mechanism 410 of the base 402 can be removably coupled to a connection mechanism 414 of a urine or moisture sensor 412. Sensor 412, with connection mechanism 414, can be disposable or washable and reusable. An example of suitable connection mechanisms 410, 414 include hook and loop fasteners, removable adhesives, mechanical fasteners, and other suitable mechanisms.

In some cases, the base 402 and the sensor 412 are permanently coupled together. The base 402 and sensor 412 may be located within a single housing or enclosure, such as a waterproof enclosure. Thus, the sensor urination detection sensor 400 can be a fully enclosed sensor containing all necessary equipment (e.g., sensor, antenna, optional battery) and circuitry necessary to perform the functions disclosed herein.

The base 402 can contain any necessary communications equipment and/or processing equipment to receive information from a sensor 412 and communicate a signal indicative of a urination event.

In some cases, no power source 404 or display 408 are present, and the sensor 400 operates in a passive mode wherein wireless signals received by the wireless antenna 406 provide sufficient power to determine whether urine or moisture is present at the sensor 412 and provide a wireless response indicative of whether urine or moisture is detected. In some cases, the sensor 400 can be disposable, in which case the base 402 may be a one-time use base (e.g., the base 402 may be not reusable and may optionally be permanently coupled to the sensor 412 or colocated with the sensor 412 within a single enclosure).

In an example, a sensor 400 can be used by associating the base 402 to a hub, application server, and/or computing device to form a communication channel. The base 402 can transmit a signal indicative of whether or not a sensor 412 is coupled to the base 402. When a sensor 412 is attached to the base 402, the sensor 400 can transmit a signal indicative of whether urine or moisture is present at the sensor 412. The sensor 400 may initially detect no urine and may be installed in a suitable location. Once the sensor 412 detects urine or moisture, the sensor 400 can transmit a signal indicative that urine or moisture has been detected. A component receiving such a signal can generate data including a timestamp and an indication that a urination event has occurred. The timestamp may be very accurate, as the signal may be nearly instantaneous. The signal received from the sensor 400 can also be used to alert the system and take appropriate action, such as generating a stimulus for a user or caregiver.

Figure 5:
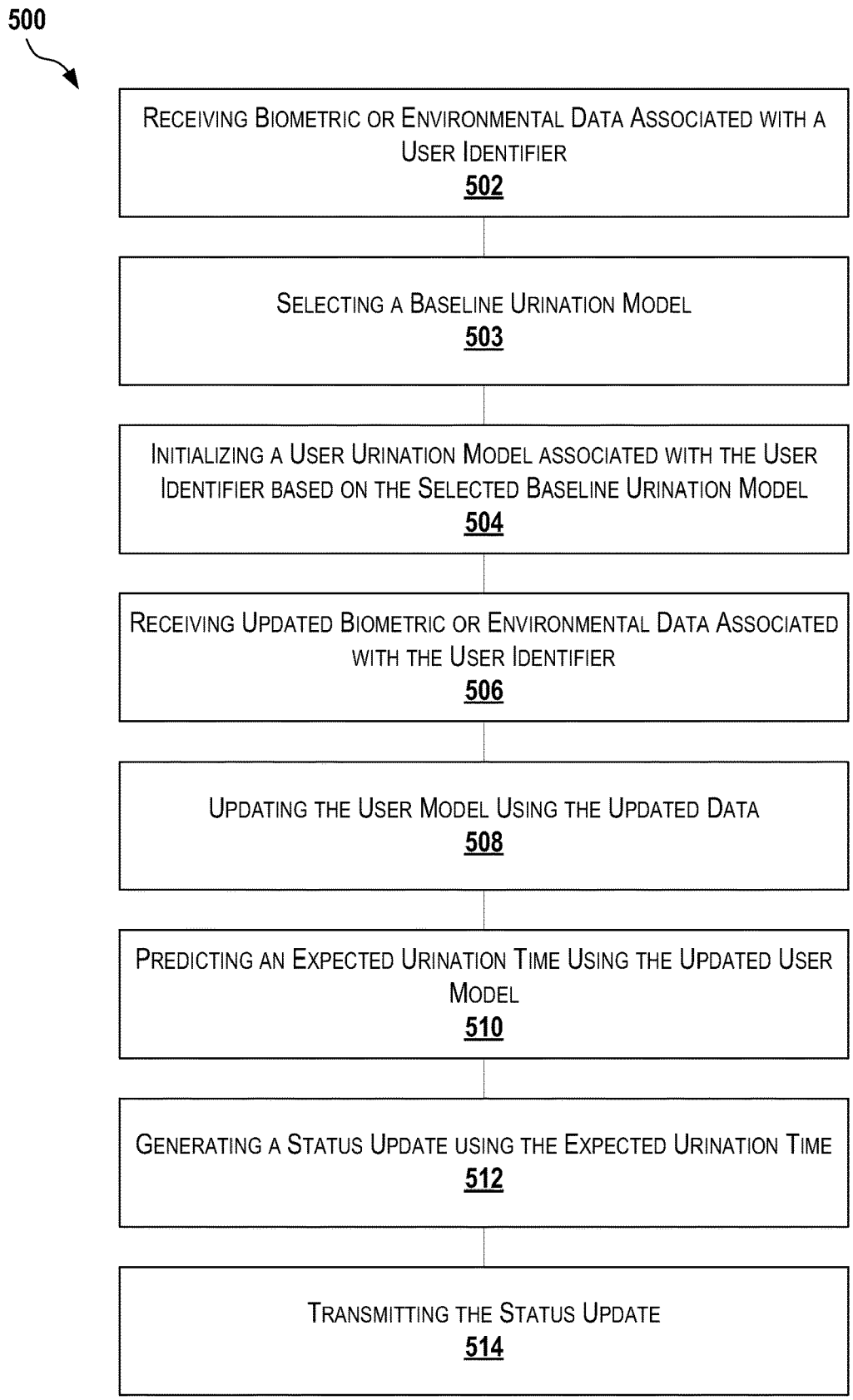
FIG. 5 is a flowchart depicting a process for initiating a urination model according to certain aspects of the present disclosure.

FIG. 5 is a flowchart depicting a process 500 for initializing and training a urination model according to certain aspects of the present disclosure. Process 500 can be performed, in whole or in part, by any suitable device, such as a wearable device, a hub, a computing device, or an application server.

At optional block 502, data (e.g., biometric and/or environmental) is received. The received data can be associated with a user identifier. As used herein, the association of any data, model, or other element with a user identifier can take many forms. In one example, data associated with a user identifier can include appending the data with the user identifier. In another example, the data can include a device identifier, which may be based on the device to which the data is transmitted, the device from which the data is received, or another device through which the data has passed. An association database can track which device identifiers are associated with a particular user identifier or multiple user identifiers. Thus, the data associated with a particular device identifier, which is in turn associated with the user identifier, may be considered as being associated with the user identifier. In some cases, an association database can track other unique identifiers and their association with a particular user identifier or multiple user identifiers, and thereby allow association of any number of unique identifiers to a particular user identifier. These unique identifiers can be data identifiers, network identifiers, or any other suitable identifier. Association databases can be stored in any suitable device, such as a wearable device, a hub, a computing device, or an application server. In some cases, some or all of an association database may be duplicated and/or synced across multiple devices in a single ecosystem (e.g., ecosystem 100 of FIG. 1). Therefore, in one example, while a main association database may be stored on an application server, a hub may nevertheless maintain at least a partial association database locally to use when connection to the application server is unavailable or when it is desirable to reduce bandwidth usage.

At block 503, a baseline urination model is selected. The baseline urination model can be selected at random or pursuant to a selection algorithm using the received data from block 502, stored data associated with the user identifier, and/or other data associated with the user identifier. At block 504, a user urination model can be initialized. Initializing the user urination model can include generating the user urination model using the baseline urination model selected at block 503. The user urination model can initially be identical to or a copy of the selected baseline urination model. When the user urination model is generated or being initialized, it can be associated with the user identifier. Thus, the user urination model can be a model for predicting expected urination times that is specific to a particular user, namely the user associated with the user identifier.

At block 506, updated data (e.g., biometric and/or environmental) is received. The updated data is associated with the user identifier of block 504 and optional block 502. At block 508, the user model is updated using the updated data received at block 506. The user model, after being updated at block 508, may be specific to the user and different from the initial predictive urination model.

At block 510, the updated user model is used to predict an expected urination time. In some cases, the updated user model can be applied to current, historical, and/or recent data to predict the expected urination time. For example, the updated user model can be applied to the updated data received at block 506, optionally including the data received at optional block 502. In some cases, block 510 can include acquiring current data, which can be used in conjunction with the updated user model to predict the expected urination time.

At block 512, a status update can be generated based on the expected urination time determined at block 510. At block 514, the status update is transmitted. The status update can be transmitted immediately (e.g., to send a message indicating when urination is expected) or can be delayed until a time soon before the expected urination time (e.g., when the status update includes a stimulus indicating that urination is imminent). The status update, when processed by a receiving device, can result in the generation of a stimulus based on or including the expected urination time. In some cases, block 514 includes presenting a stimulus at the device performing process 500.

Figure 6:
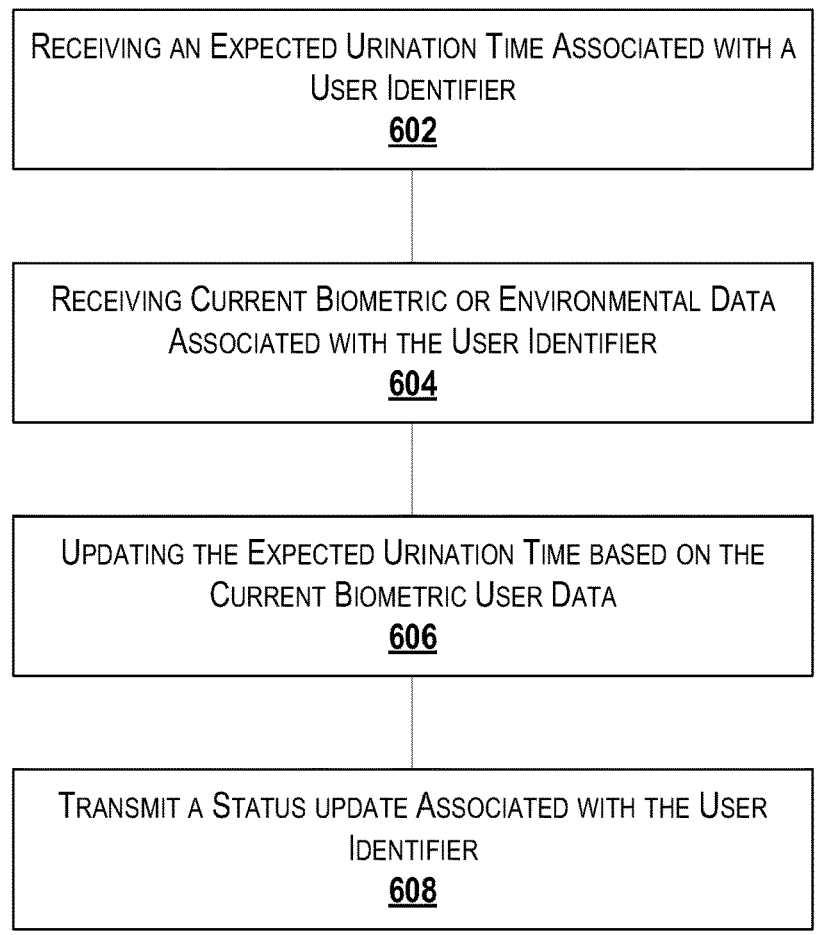
FIG. 6 is a flowchart depicting a process for updating an expected urination time according to certain aspects of the present disclosure.

FIG. 6 is a flowchart depicting a process 600 for updating an expected urination time according to certain aspects of the present disclosure. Process 600 can be performed, in whole or in part, by any suitable device, such as a wearable device, a hub, a computing device, or an application server.

At block 602, an expected urination time is received. The expected urination time can be received from the device performing process 600 or another device. The expected urination time can be associated with a user identifier.

At block 604, current data (e.g., biometric or environmental) associated with the user identifier is received (e.g., from the device performing process 600 or another device). At block 606, the expected urination time from block 602 is updated based on the current data received at block 604.

At optional block 608, a status update can be transmitted. The status update can be associated with the user identifier and can be transmitted to a device associated with the user identifier (e.g., a user's or caregiver's device). When received, the status update can facilitate or induce generation of a stimulus (e.g., a vibration, a sound, a visual stimulus, or any other suitable direct or environmental stimulus). The stimulus can be based on or can include the updated expected urination time. In some cases, at block 608, the device performing process 600 can generate the stimulus.

Figure 7:
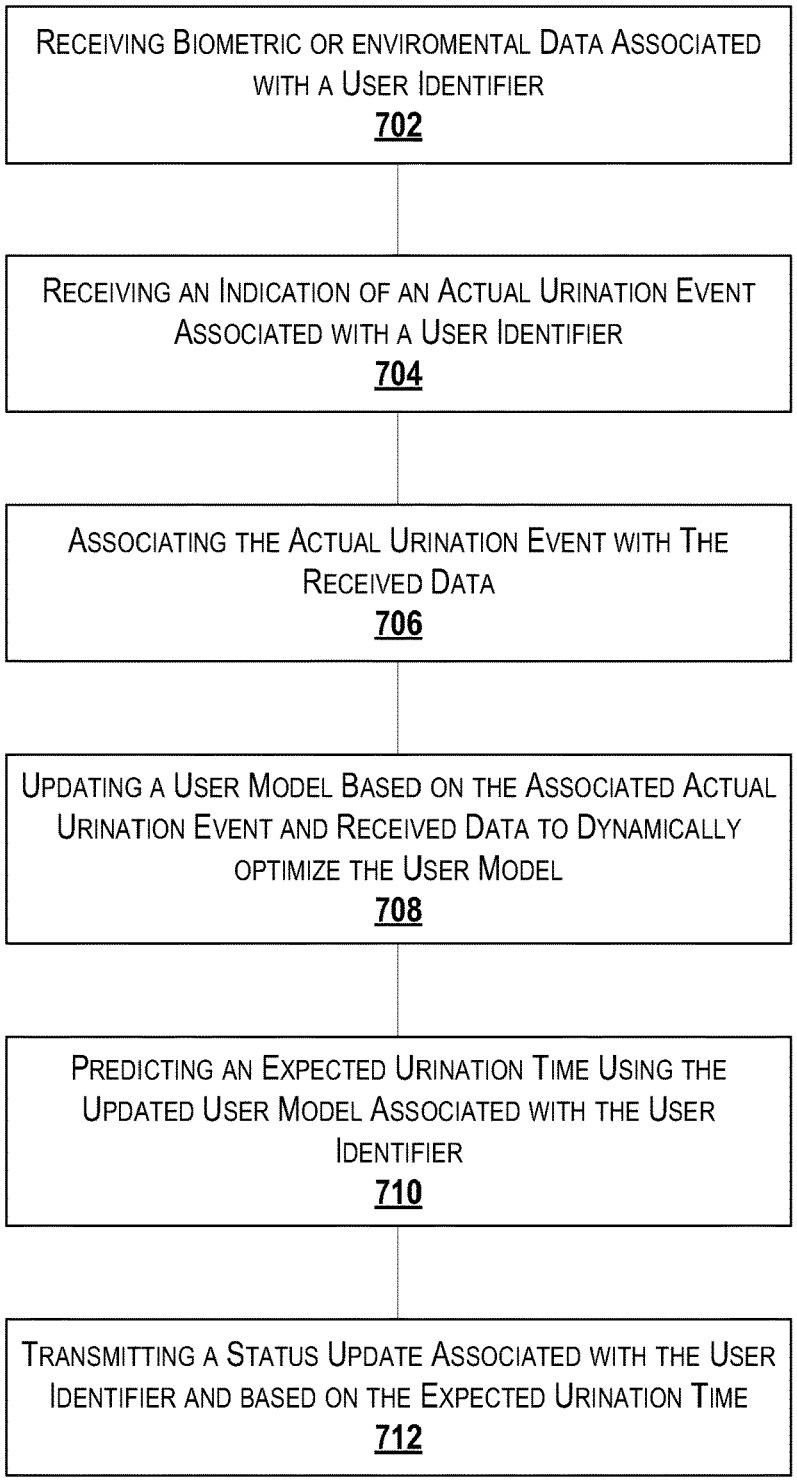
FIG. 7 is a flowchart depicting a process for updating a urination model according to certain aspects of the present disclosure.

FIG. 7 is a flowchart depicting a process 700 for updating a urination model according to certain aspects of the present disclosure. Process 700 can be performed, in whole or in part, by any suitable device, such as a wearable device, a hub, a computing device, or an application server.

At block 702, data (e.g., biometric or environmental) is received. The data can originate at and be received from the device performing process 700 or another device. The data can be associated with a user identifier.

At block 704, an indication of an actual urination event associated with the user identifier is received. The indication can be in the form of a signal received from a urination detection sensor. The indication can be in the form of a feedback signal, such as a voluntary or involuntary feedback signal. The indication can originate at and be received from the device performing process 700 or another device.

At block 706, the actual urination event is associated with the data received at block 702 using the indication received at block 704. Timestamp data can be used to associate the actual urination event with a proper subset of data from the received data of block 702.

At block 708, a user model is updated based on the associated actual urination event and the received data. Updating the user model can include optimizing the user model. Optimizing the user model can include updating the model so that the received data associated with the actual urination event at block 706 provides a stronger prediction of a urination event when processed using the user model after the update than when processed using the user model prior to the update. In some cases, block 708 can include receiving the updated user model, which may be generated by a device other than the one performing process 700.

At block 710, the updated user model is used to predict an expected urination time. In some cases, the updated user model can be applied to current, historical, and/or recent data to predict the expected urination time. For example, the updated user model can be applied to the data received at block 702. In some cases, block 710 can include acquiring current data, which can be used in conjunction with the updated user model to predict the expected urination time.

At block 712, a status update is transmitted based on the expected urination time determined at block 710. The status update can be transmitted immediately (e.g., to send a message indicating when urination is expected) or can be delayed until a time soon before the expected urination time (e.g., when the status update includes a stimulus indicating that urination is imminent). The status update, when processed by a receiving device, can result in the generation of a stimulus based on or including the expected urination time. In some cases, block 712 includes presenting a stimulus at the device performing process 700.

Figure 8:
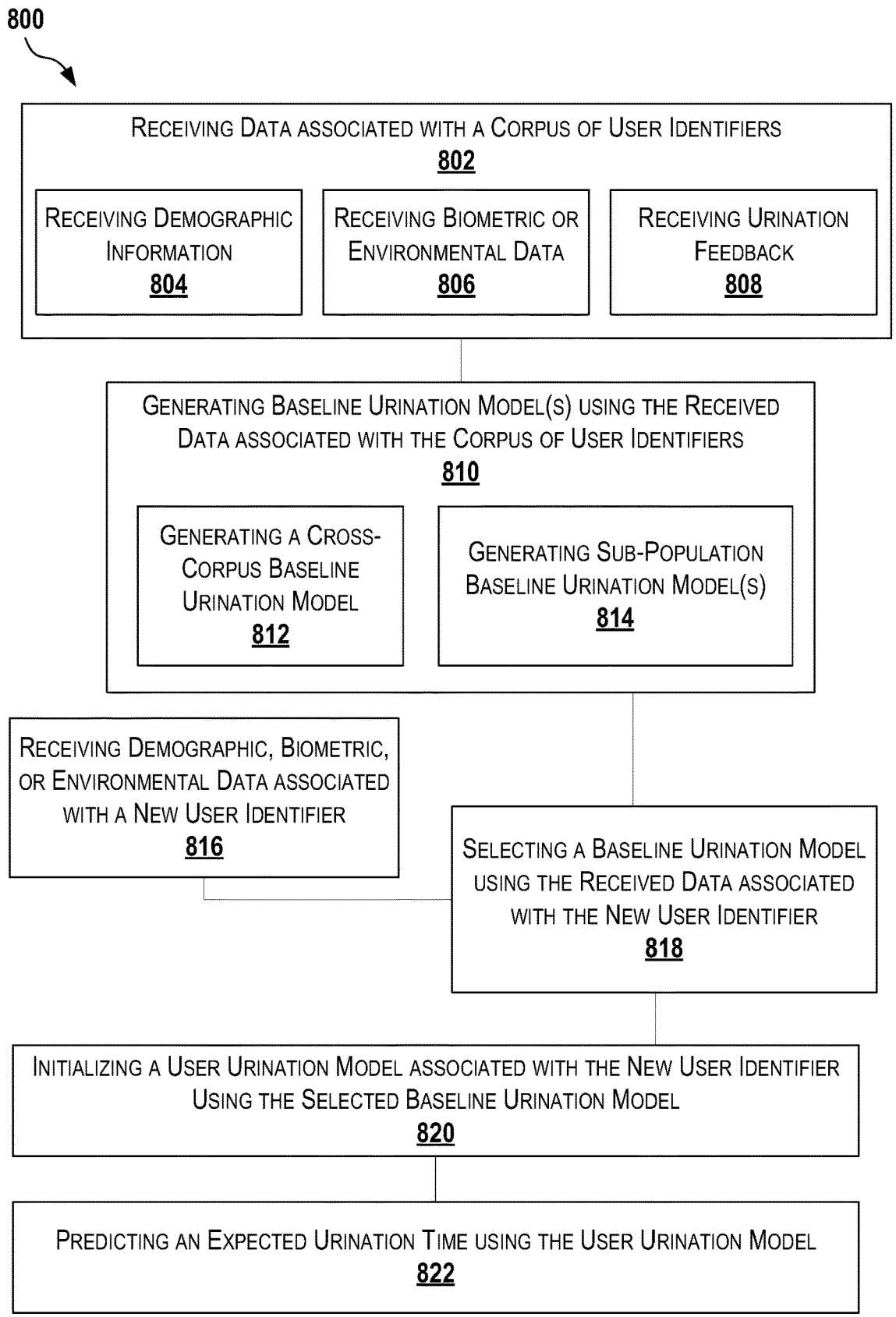
FIG. 8 is a flowchart depicting a process for generating baseline urination models and initializing user urination models according to certain aspects of the present disclosure.

FIG. 8 is a flowchart depicting a process 800 for generating baseline urination models and initializing user urination models according to certain aspects of the present disclosure. Process 800 can be performed, in whole or in part, by any suitable device, such as a wearable device, a hub, a computing device, or an application server. Process 800 may be beneficially performed by a device suitable for receiving data associated with multiple user identifiers, and thus may be beneficially performed on an application server.

At block 802, data associated with a corpus of user identifiers can be received. The data can include multiple individual data items, each associated with one of a collection of user identifiers in a corpus of user identifiers. Thus, a dataset of data can be generated, including data from many different users associated with many different user identifiers. Receiving data at block 802 can include one or more of blocks 804, 806, 808. At block 804, demographic information is received. At block 806, biometric and/or environmental data is received. At block 808, urination feedback (e.g., voluntary or involuntary) is received. At all of block 804, 806, 808, the data received (e.g., demographic information, biometric and/or environmental data, and/or urination feedback) can be associated with user identifiers.

At block 810, one or more baseline urination models can be generated using the data received at block 802 (e.g., at blocks 804, 806, 808). Generating a baseline urination model can include processing the data associated with multiple user identifiers to generate a predictive model that well-predicts (e.g., optimally predicts) a given outcome (e.g., a urination event) given the data associated with those user identifiers. Thus, the baseline urination model may not be the most optimal prediction model for a particular user, it may be an optimal prediction model for all of the users from which the model is generated.

Generating a baseline urination model at block 810 can include generating a cross-corpus baseline urination model at block 812. The cross-corpus baseline urination model can represent a desirable or optimal prediction model for all of the data associated with each of the user identifiers in the corpus of user identifiers. In other words, the cross-corpus baseline urination model can represent the optimal model trained on the data from all users for which data is received.

Optionally, additionally or alternatively, generating a baseline urination model at block 810 can include generating one or more sub-population baseline urination models at block 814. A sub-population baseline urination model can represent a desirable or optimal prediction model for all of the data associated with a sub-population of user identifiers of the corpus of user identifiers. In other words, the sub-population baseline urination model can represent the optimal model trained on the data from a subset of the users for which data is received. Generating sub-population baseline urination models can include establishing sub-populations by intelligently grouping user identifiers based on any suitable algorithm, such as clustering algorithms. Thus, a sub-population can represent a collection of user identifiers (e.g., fewer than all user identifiers of the corpus) for which a urination event can be predicted with high accuracy according to a particular sub-population baseline urination model. A sub-population can be established (e.g., intelligently grouped) based on any of the data received at block 802.

In a first example, a sub-population may be established using biometric data received at block 806. It may be determined, through machine learning and intelligent grouping, that individuals with average resting heart rates above a predetermined limit and/or average skin conductivity at or below a certain predetermined limit may be well-modeled using one particular sub-population baseline urination model (e.g., a model that provides a greater weight to a skin conductivity variable). In a second example, a sub-population may be established using environmental data received at block 806. It may be determined, through machine learning and intelligent grouping, that individuals that spend more than a certain number of hours each day in environments having at least a certain minimum ambient temperature and/or having less than a certain maximum humidity, may be well-modeled using a particular sub-population baseline urination model (e.g., a model that delays urination time predictions more than other models or more than a cross-corpus baseline urination model). In some cases, demographic information may be especially useful for grouping sub-populations.

At block 816, demographic, biometric, and/or environmental data associated with a new user identifier can be received. At block 818, the data received at block 816 that is associated with the new user identifier can be used to select an appropriate (e.g., having a high likelihood of accuracy) baseline urination model. In some cases, if no data is received at block 818, the cross-corpus baseline urination model can be automatically selected. In some cases, if the data received at block 816 does not match or fit with any sub-populations of block 814, the cross-corpus baseline urination model can be selected. However, if some or all of the data received at block 816 matches or fits with any of the sub-populations of block 814, the sub-population baseline urination model of the best-fit sub-population can be selected.

For example, if the data associated with the new user identifier shows average resting heart rates above a predetermined limit and/or average skin conductivity at or below a certain predetermined limit described above with reference to the first example, the user identifier may be associated with the sub-population of that first example and the sub-population baseline urination model of that first example may be selected. In another example, if the data associated with the new user identifier shows that the user associated with the user identifier spends more than a certain number of hours each day in environments having at least a certain minimum ambient temperature and/or having less than a certain maximum humidity, the user identifier may be associated with the sub-population of that second example and the sub-population baseline urination model of that second example may be selected. In yet another example, if the data associated with the new user identifier fits with both the sub-population of the first example and the sub-population of the second example, a determination can be made as to which of the two sub-populations is a better fit, and the sub-population baseline urination model for that sub-population can be used.

In some cases in which data from a new user identifier can fit with more than a single sub-population, the baseline urination model selected at block 818 can be a combined, optionally new, baseline urination model representing average or otherwise combined traits of the individual sub-population baseline urination models of the matching or fitting sub-populations.

At block 820, a user urination model can be initialized. Initializing the user urination model can include generating the user urination model using the baseline urination model selected at block 818. The user urination model can initially be identical to or a copy of the selected baseline urination model. When the user urination model is generated or being initialized, it can be associated with the new user identifier. Thus, the user urination model can be a model for predicting expected urination times that is specific to a particular user, namely the user associated with the user identifier.

At block 822, the user urination model can be used to predict an expected urination time associated with the user identifier. In some cases, the user urination model can be applied to current, historical, and/or recent data to predict the expected urination time. For example, the updated user model can be applied to the data received at block 816. In some cases, block 822 can include acquiring current data, which can be used in conjunction with the user urination model to predict the expected urination time.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

As used below, any reference to a series of examples is to be understood as a reference to each of those examples disjunctively (e.g., "Examples 1-4" is to be understood as "Examples 1, 2, 3, or 4").

Example 1 is a system, comprising: one or more data processors; and a non-transitory computer-readable storage medium containing instructions which, when executed on the one or more data processors, cause the one or more data processors to perform operations including: receiving biometric data associated with a unique identifier; accessing a urination prediction model associated with the unique identifier; generating an updated urination prediction model using the received biometric data; predicting an expected urination time using the updated urination prediction model and the received biometric data; and generating a status update using the expected urination time and the unique identifier, wherein generating the status update facilitates generation of a stimulus.

Example 2 is the system of example 1, wherein the operations further include transmitting the status update, and wherein the status update facilitates generation of the stimulus when received.

Example 3 is the system of example 2, wherein transmitting the status update includes appending the status update with the unique identifier or a device identifier associated with the unique identifier, and wherein the status update, when received by an intermediate device, induces the intermediate device to forward the status update to a subsequent device associated with the unique identifier.

Example 4 is the system of examples 1-3, wherein the operations further include: receiving demographic information associated with the unique identifier; selecting a baseline model using the received demographic information; and initializing the urination prediction model using a baseline model.

Example 5 is the system of examples 1-4, wherein the operations further include receiving a feedback signal associated with the unique identifier, wherein the feedback signal is indicative of an occurrence of a urination event, and wherein generating the updated urination prediction model includes applying a machine learning technique to the urination prediction model using the feedback signal and the received biometric data.

Example 6 is the system of example 5, wherein the operations further include transmitting a feedback request signal, wherein the feedback request signal induces generation of a feedback request stimulus when received.

Example 7 is a computer-implemented method, comprising: receiving, by a computing device, biometric data associated with a unique identifier; accessing, a urination prediction model associated with the unique identifier; generating an updated urination prediction model using the received biometric data; predicting an expected urination time using the updated urination prediction model and the received biometric data; and generating a status update using the expected urination time and the unique identifier, wherein generating the status update facilitates generation of a stimulus.

Example 8 is the method of example 7, further comprising transmitting the status update, and wherein the status update facilitates generation of the stimulus when received.

Example 9 is the method of example 8, wherein transmitting the status update includes appending the status update with the unique identifier or a device identifier associated with the unique identifier, and wherein the status update, when received by an intermediate device, induces the intermediate device to forward the status update to a subsequent device associated with the unique identifier.

Example 10 is the method of examples 7-9, further comprising: receiving demographic information associated with the unique identifier; selecting a baseline model using the received demographic information; and initializing the urination prediction model using a baseline model.

Example 11 is the method of examples 7-9, further comprising receiving a feedback signal associated with the unique identifier, wherein the feedback signal is indicative of an occurrence of a urination event, and wherein generating the updated urination prediction model includes applying a machine learning technique to the urination prediction model using the feedback signal and the received biometric data.

Example 12 is the method of example 11, further comprising transmitting a feedback request signal, wherein the feedback request signal induces generation of a feedback request stimulus when received.

Example 13 is a computer-program product tangibly embodied in a non-transitory machine-readable storage medium, including instructions configured to cause a data processing apparatus to perform operations including: receiving biometric data associated with a unique identifier; accessing a urination prediction model associated with the unique identifier; generating an updated urination prediction model using the received biometric data; predicting an expected urination time using the updated urination prediction model and the received biometric data; and generating a status update using the expected urination time and the unique identifier, wherein generating the status update facilitates generation of a stimulus.

Example 14 is the computer-program product of example 13, wherein the operations further include transmitting the status update, and wherein the status update facilitates generation of the stimulus when received.

Example 15 is the computer-program product of example 14, wherein transmitting the status update includes appending the status update with the unique identifier or a device identifier associated with the unique identifier, and wherein the status update, when received by an intermediate device, induces the intermediate device to forward the status update to a subsequent device associated with the unique identifier.

Example 16 is the computer-program product of examples 13-15, wherein the operations further include: receiving demographic information associated with the unique identifier; selecting a baseline model using the received demographic information; and initializing the urination prediction model using a baseline model.

Example 17 is the computer-program product of examples 13-16, wherein the operations further include receiving a feedback signal associated with the unique identifier, wherein the feedback signal is indicative of an occurrence of a urination event, and wherein generating the updated urination prediction model includes applying a machine learning technique to the urination prediction model using the feedback signal and the received biometric data.

Example 18 is the computer-program product of example 17, wherein the operations further include transmitting a feedback request signal, wherein the feedback request signal induces generation of a feedback request stimulus when received.

Example 19 is the system of examples 1-6, wherein the biometric data includes heart rate variability.

Example 20 is the system of examples 1-6 or 20, wherein the biometric data excludes a measurement of bladder fullness.

Example 21 is the system of examples 1-6, 20, or 21, wherein the operations further comprise selecting a baseline model using the biometric data; and initializing the urination prediction model using the baseline model. In some cases, the operations can instead comprise receiving additional biometric data; selecting a baseline model using the additional biometric data; and initializing the urination prediction model using the baseline model.

Example 22 is the method of examples 7-12, wherein the biometric data includes heart rate variability.

Example 23 is the method of examples 7-12 or 22, wherein the biometric data excludes a measurement of bladder fullness.

Example 24 is the method of examples 7-12, 22, or 23, further comprising selecting a baseline model using the biometric data; and initializing the urination prediction model using the baseline model. In some cases, the operations can instead comprise receiving additional biometric data; selecting a baseline model using the additional biometric data; and initializing the urination prediction model using the baseline model.

Example 25 is the computer-program product of examples 13-18, wherein the biometric data includes heart rate variability.

Example 26 is the computer-program product of examples 13-18 or 23, wherein the biometric data excludes a measurement of bladder fullness.

Example 27 is the computer-program product of examples 13-18, 25, or 26, wherein the operations further comprise selecting a baseline model using the biometric data; and initializing the urination prediction model using the baseline model. In some cases, the operations can instead comprise receiving additional biometric data; selecting a baseline model using the additional biometric data; and initializing the urination prediction model using the baseline model.

What is claimed is:

1. A system, comprising:
    one or more data processors; and
    a non-transitory computer-readable storage medium containing instructions which, when executed on the one or more data processors, cause the one or more data processors to perform operations including:
        receiving biometric data associated with a unique identifier, wherein the received biometric data is heart rate data, ambient temperature data, body temperature data, blood oxygenation data, skin conductivity data, blood pressure data, electrocardiogram data, electroencephalogram data, electromyographic data, respiration rate data, sleep quality data, depth of sleep data, restfulness data, heart rate variability data, or combinations thereof, and wherein the biometric data does not include a bladder measurement;
        accessing a urination prediction model associated with the unique identifier;
        generating an updated urination prediction model using the received biometric data;
        predicting an expected urination time using the updated urination prediction model and the received biometric data, wherein predicting the expected urination time occurs without measuring a bladder; and
        generating a status update using the expected urination time and the unique identifier, wherein generating the status update facilitates generation of a stimulus at a user computing device and generation of an additional stimulus at a caregiver computing device.

2. The system of claim 1, wherein the operations further include transmitting the status update, wherein the status update facilitates generation of the stimulus when received, wherein transmitting the status update includes appending the status update with the unique identifier or a device identifier associated with the unique identifier, and wherein the status update, when received by an intermediate device, induces the intermediate device to forward the status update to the caregiver computing device.

3. The system of claim 1, wherein the operations further include:
    receiving demographic information associated with the unique identifier, wherein the demographic information is indicative of a population of users;
    selecting a baseline model from a set of potential baseline models using the received demographic information, wherein the selected baseline model is trained using historical data collected over time from the population of users; and
    generating the urination prediction model using the baseline model.

4. The system of claim 1, wherein the operations further include:
    selecting a baseline model from a set of potential baseline models using the biometric data, wherein each of set of potential baseline models is trained using historical data collected over time from respective populations of users; and
    generating the urination prediction model using the baseline model.

5. The system of claim 1, wherein the received biometric data comprises heart rate data, heart rate variability data, or a combination thereof.

6. The system of claim 1, wherein the operations further comprise:
    receiving feedback in response to generation of the stimulus, wherein the feedback is associated with a need to urinate at the time the stimulus is generated; and
    further updating the updated urination prediction model based on the feedback.

7. A computer-implemented method, comprising:
    receiving, by a computing device, biometric data associated with a unique identifier, wherein the received biometric data is heart rate data, ambient temperature data,-body temperature data, blood oxygenation data, skin conductivity data, blood pressure data, electrocardiogram data, electroencephalogram data, electromyographic data, respiration rate data, sleep quality data, depth of sleep data, restfulness data, heart rate variability data, or combinations thereof, and wherein the biometric data does not include a bladder measurement;
    accessing a urination prediction model associated with the unique identifier;
    generating an updated urination prediction model using the received biometric data;
    predicting an expected urination time using the updated urination prediction model and the received biometric data, wherein predicting the expected urination time occurs without measuring a bladder; and
    generating a status update using the expected urination time and the unique identifier, wherein generating the status update facilitates generation of a stimulus at a user computing device and generation of an additional stimulus at a caregiver computing device.

8. The method of claim 7, further comprising transmitting the status update, wherein the status update facilitates generation of the stimulus when received, wherein transmitting the status update includes appending the status update with the unique identifier or a device identifier associated with the unique identifier, and wherein the status update, when received by an intermediate device, induces the intermediate device to forward the status update to the caregiver computing device.

9. The method of claim 7, further comprising:
receiving demographic information associated with the unique identifier, wherein the demographic information is indicative of a population of users;
selecting a baseline model from a set of potential baseline models using the received demographic information, wherein the selected baseline model is trained using historical data collected over time from the population of users; and
generating the urination prediction model using the baseline model.

10. The method of claim 7, further comprising:
selecting a baseline model from a set of potential baseline models using the biometric data, wherein each of set of potential baseline models is trained using historical data collected over time from respective populations of users; and
generating the urination prediction model using the baseline model.

11. The method of claim 7, wherein the received biometric data comprises heart rate data, heart rate variability data, or a combination thereof.

12. The method of claim 7, further comprising:
receiving feedback in response to generation of the stimulus, wherein the feedback is associated with a need to urinate at the time the stimulus is generated; and
further updating the updated urination prediction model based on the feedback.

13. A computer-program product tangibly embodied in a non-transitory machine-readable storage medium, including instructions configured to cause a data processing apparatus to perform operations including:
receiving biometric data associated with a unique identifier, wherein the received biometric data is heart rate data, ambient temperature data, body temperature data, blood oxygenation data, skin conductivity data, blood pressure data, electrocardiogram data, electroencephalogram data, electromyographic data, respiration rate data, sleep quality data, depth of sleep data, restfulness data, heart rate variability data, or combinations thereof, and wherein the biometric data does not include a bladder measurement;
accessing a urination prediction model associated with the unique identifier;
generating an updated urination prediction model using the received biometric data;
predicting an expected urination time using the updated urination prediction model and the received biometric data, wherein predicting the expected urination time occurs without measuring a bladder; and
generating a status update using the expected urination time and the unique identifier, wherein generating the status update facilitates generation of a stimulus at a user computing device and generation of an additional stimulus at a caregiver computing device.

14. The computer-program product of claim 13, wherein the operations further comprise transmitting the status update, wherein the status update facilitates generation of the stimulus when received, wherein transmitting the status update includes appending the status update with the unique identifier or a device identifier associated with the unique identifier, and wherein the status update, when received by an intermediate device, induces the intermediate device to forward the status update the caregiver computing device.

15. The computer-program product of claim 13, wherein the operations further include:
receiving demographic information associated with the unique identifier, wherein the demographic information is indicative of a population of users;
selecting a baseline model from a set of potential baseline models using the received demographic information, wherein the selected baseline model is trained using historical data collected over time from the population of users; and
generating the urination prediction model using the baseline model.

16. The computer-program product of claim 13, wherein the operations further include:
selecting a baseline model from a set of potential baseline models using the biometric data, wherein each of set of potential baseline models is trained using historical data collected over time from respective populations of users; and
generating the urination prediction model using the baseline model.

17. The computer-program product of claim 13, wherein the received biometric data comprises heart rate data, heart rate variability data, or a combination thereof.

18. The computer-program product of claim 13, wherein the operations further comprise:
receiving feedback in response to generation of the stimulus, wherein the feedback is associated with a need to urinate at the time the stimulus is generated; and
further updating the updated urination prediction model based on the feedback.

19. The system of claim 1, wherein the operations further include:
predicting an expected urge to micturate time using the updated urination prediction model and at least one of the biometric data and additional biometric data; and
generating an additional status update using the predicted expected urge to micturate time and the unique identifier, wherein generating the additional status update facilitates generation of a secondary stimulus at the user computing device.

20. The method of claim 7, further comprising:
predicting an expected urge to micturate time using the updated urination prediction model and at least one of the biometric data and additional biometric data; and
generating an additional status update using the predicted expected urge to micturate time and the unique identifier, wherein generating the additional status update facilitates generation of a secondary stimulus at the user computing device.

21. The computer-program product of claim 13, wherein the operations further include:
predicting an expected urge to micturate time using the updated urination prediction model and at least one of the biometric data and additional biometric data; and
generating an additional status update using the predicted expected urge to micturate time and the unique identifier, wherein generating the additional status update facilitates generation of a secondary stimulus at the user computing device.

* * * * *